United States Patent
Harding

(10) Patent No.: US 8,582,718 B2
(45) Date of Patent: Nov. 12, 2013

(54) METHOD AND SYSTEM FOR DERIVING MOLECULAR INTERFERENCE FUNCTIONS FROM XRD PROFILES

(75) Inventor: Geoffrey Harding, Hamburg (DE)

(73) Assignee: Morpho Detection, Inc., Newark, CA (US)

( * ) Notice: Subject to any disclaimer, the term of this patent is extended or adjusted under 35 U.S.C. 154(b) by 410 days.

(21) Appl. No.: 12/956,715

(22) Filed: Nov. 30, 2010

(65) Prior Publication Data

US 2012/0133516 A1    May 31, 2012

(51) Int. Cl.
*G01N 23/06*    (2006.01)
(52) U.S. Cl.
USPC .................. 378/53; 378/49; 378/36; 340/600
(58) Field of Classification Search
USPC ........... 378/36, 49, 53, 70, 71, 82, 83, 86, 88, 378/90, 92; 340/600
See application file for complete search history.

(56) References Cited

U.S. PATENT DOCUMENTS

| | | | |
|---|---|---|---|
| 7,499,523 B2 | 3/2009 | Harding | |
| 7,519,154 B2 | 4/2009 | Harding | |
| 7,529,340 B2 | 5/2009 | Harding | |
| 7,587,026 B2 | 9/2009 | Harding | |
| 7,697,664 B2 | 4/2010 | Harding | |
| 7,711,086 B2 | 5/2010 | Harding | |
| 7,738,729 B2 | 6/2010 | Harding | |
| 7,764,764 B2 | 7/2010 | Harding | |
| 2008/0080670 A1 | 4/2008 | Harding | |
| 2009/0166551 A1 | 7/2009 | Harding et al. | |
| 2009/0168958 A1 | 7/2009 | Cozzini et al. | |
| 2009/0168962 A1 | 7/2009 | Harding | |
| 2009/0168963 A1 | 7/2009 | Harding | |
| 2009/0228216 A1 | 9/2009 | Harding | |
| 2010/0111255 A1 | 5/2010 | Harding | |
| 2010/0124315 A1 | 5/2010 | Harding | |

OTHER PUBLICATIONS

PCT International Search Report and Written Opinion of the International Searching Authority mailed Mar. 26, 2012 regarding PCT/US2011/062212 filed on Nov. 28, 2011; 20 pages.

Zou, K. et al. Correlation and Simple Linear Regression. Published Online 1-20, 25 10.1148/radiol.2273011499. vol. 227. No. 3. Radiology. 2003. 227:617-628. [Retrieved on Mar. 12, 20121. Retrieved from Internet: URL: <http://radiology.rsna.org/content/227/3/617.full.pdf > entire document.

Larsen, P. Master of applied statistics. Regression and analysis of variance. Module 4. 12 Feb. 1-26, 2008. [Retrieved on Mar. 12, 2012]. Retrieved from internet: URL: <http://statmaster.sdu.dk/courses/stl11/module04/module.pdf > entire document.

*Primary Examiner* — Eric M Blount
(74) *Attorney, Agent, or Firm* — Armstrong Teasdale LLP

(57) ABSTRACT

A method for identifying a substance includes determining a first molecular interference function (MIF) for a first substance. The method also includes determining a second MIF for a second substance. The method further includes generating a residual MIF at least partially based on a comparison of the second MIF to the first MIF. The method also includes identifying the type of substance based on the residual MIF.

26 Claims, 13 Drawing Sheets

| Moment | Cola | Cognac | Sun cream | Fuel - water mix |
|---|---|---|---|---|
| Zero | 0.03 | 0.05 | 0.06 | 0.25 |
| First | 1.25 | 1.23 | 1.11 | 1.15 |
| Second | 0.080 | 0.047 | 0.048 | 0.046 |
| Third | 0.029 | -0.001 | 0.007 | -0.013 |
| Fourth | 0.050 | 0.015 | 0.017 | 0.013 |

METHOD AND SYSTEM FOR DERIVING MOLECULAR INTERFERENCE FUNCTIONS FROM XRD PROFILES

BACKGROUND OF THE INVENTION

1. Field of the Invention

The embodiments described herein relate generally to a method and system for characterizing a substance and, more particularly, to a method and system for deriving a molecular interference function (MIF) of a liquid, amorphous substance, or gel from an X-ray diffraction (XRD) profile of the material.

2. Description of Related Art

Many known security systems for screening materials include a substance identification system that is configured with x-ray beam detection technology employing known x-ray diffraction (XRD) devices and methods. Many of these known XRD devices include at least one x-ray source to generate a single x-ray beam having a predetermined range of photon energies. Such security systems generate a diffraction profile of each substance irradiated with x-rays. Because such materials typically have a known and discernible XRD signature, detection, and identification of contraband items and substances is facilitated.

Identification of liquid, amorphous substances, and gel substances, sometimes referred to as LAGs, in security screening relies in part on determining an associated molecular interference function (MIF) for each substance. This, in turn, depends on estimating an effective atomic number of a scatter sample, that is, the x-rays scattered from at least a portion of an irradiated sample. At least some known XRD screening systems use a High Energy Tip Region Analysis (HETRA) method. However, using HETRA methods, regions of the resultant XRD profile are determined at relatively high momentums to accurately determine the mean atomic number. In such high momentum regions of the XRD profile, the signal strength is relatively low compared to the associated photon noise in the same region. Therefore, the resultant low signal-to-noise ratio may contribute to a decrease in detection rates of contraband substances and an increase in false alarms, generating uncertain results. Moreover, a large percentage of liquids, amorphous substances, and gels encountered in air passenger luggage are water-based, that is, aqueous in nature. This is at least partially due to the ease with which water, sometimes referred to as a "universal solvent", is typically mixed with a wide range of additive substances.

BRIEF SUMMARY OF THE INVENTION

In one aspect, a method for identifying a substance is provided. The method includes determining a first molecular interference function (MIF) for a first substance. The method also includes determining a second MIF for a second substance. The method further includes generating a residual MIF at least partially based on a comparison of the second MIF to the first MIF. The method also includes identifying the type of substance based on the residual MIF.

In another aspect, a method of operating a security system is provided. The method includes irradiating a substance with x-rays. The method also includes determining momentum transfer values of x-rays scattered from the substance. The method further includes generating a residual molecular interference function (MIF) for the substance that is at least partially based on the momentum transfer values. The method also includes identifying the substance based on the generated residual MIF for the substance.

In still another aspect, a substance determination system is provided. The system includes a processor coupled to at least one x-ray detector element. The processor is programmed to determine at least one of a first molecular interference function (MIF) for a first substance and determine a second MIF for a second substance. The processor is also programmed to generate a residual MIF at least partially based on a comparison of the second MIF to the first MIF. The system also includes a display device coupled to the processor. The display device is configured to identify the second substance based on the residual MIF. The system further includes at least one memory device coupled to the processor. The memory device is configured to store at least one of the first MIF, the second MIF, and the residual MIF.

In yet another aspect, a security system is provided. The security system includes an x-ray source configured to generate x-rays. The security system also includes a detector configured to detect primary and coherent scatter after the x-rays pass through a substance. The security system further includes a processor coupled to the detector. The processor is programmed to determine at least one of a first molecular interference function (MIF) for a first substance and determine a second MIF for a second substance. The processor is also programmed to generate a residual MIF at least partially based on a comparison of the second MIF to the first MIF. The security system also includes a display device coupled to the processor. The display device is configured to identify the second substance based on the residual MIF.

BRIEF DESCRIPTION OF THE DRAWINGS

FIG. 1 is a schematic view of an exemplary security system.

FIG. 2 is a schematic view of an exemplary substance determination system that may be used with the security system shown in FIG. 1.

FIG. 3 is a flow chart of an exemplary method of screening a substance using the security system shown in FIG. 1.

FIG. 4 is a flow chart of an exemplary method of determining a substance using the substance determination system shown in FIG. 2.

FIG. 5 is a graphical view of a comparison of a scatter function curve for nitrogen calculated using an Independent Atom Model (IAM) and a scatter function curve calculated using a triangular IAM approximation for nitrogen generated by the security system shown in FIG. 1.

FIG. 6 is a graphical view of an x-ray diffraction (XRD) profile curve of water generated by the security system shown in FIG. 1 and a best-fit normalized regression line derived from the XRD profile.

FIG. 7 is a graphical view of an approximated molecular interference function (MIF) curve for water using the curve and best-fit normalized regression line shown in FIG. 6.

FIG. 8 is a graphical view of an approximated MIF curve for number 2 diesel fuel generated by the security system shown in FIG. 1.

FIG. 9 is a graphical view of an approximated MIF curve for cognac, the approximated MIF curve for water shown in FIG. 7, and a residual MIF curve for cognac derived therefrom using the security system shown in FIG. 1.

FIG. 10 is a graphical view of an approximated MIF curve for a cola beverage, the approximated MIF curve for water shown in FIG. 7, and a residual MIF curve for the cola beverage derived therefrom using the security system shown in FIG. 1.

FIG. 11 is a graphical view of an approximated MIF curve for sun cream, the approximated MIF curve for water shown in FIG. 7, and a residual MIF curve for the sun cream derived therefrom using the security system shown in FIG. 1.

FIG. 12 is a graphical view of an approximated MIF curve for a diesel fuel-water mixture, the approximated MIF curve for water shown in FIG. 7, and a residual MIF curve for the diesel fuel-water mixture derived therefrom using the security system shown in FIG. 1.

FIG. 13 is a table of central moments of a plurality of substances and the associated residual MIFs derived using the security system shown in FIG. 1.

DETAILED DESCRIPTION OF THE INVENTION

Figure 1:
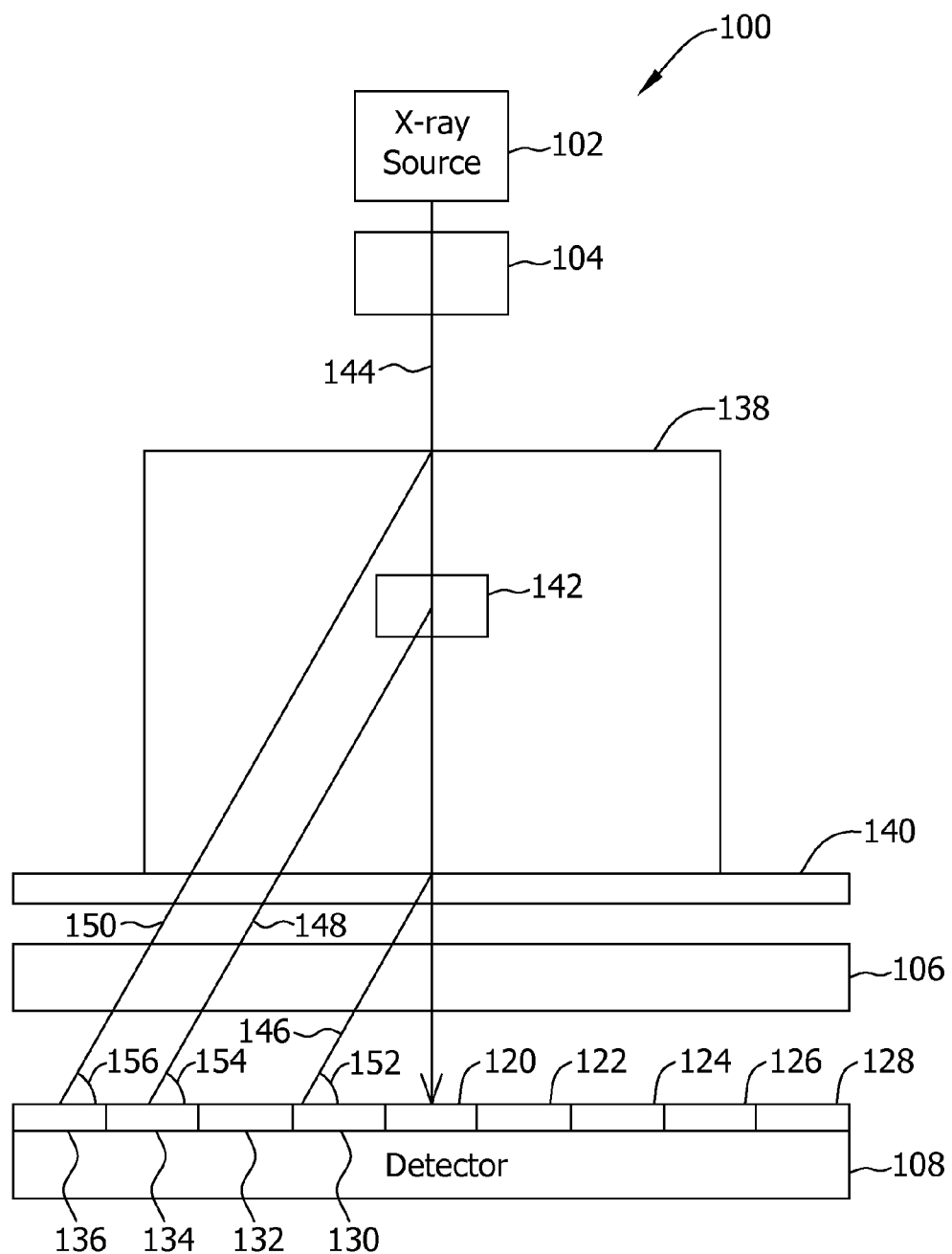
FIGS. 1-12 show exemplary embodiments of the security screening devices, systems, and methods described herein.

Embodiments of the methods and systems described herein facilitate effective and efficient operation of a security system by increasing detection rates of contraband substances and decreasing false alarm rates of non-contraband substances. The methods and systems derive molecular interference functions (MIFs) from x-ray diffraction (XRD) profiles of liquid, amorphous substances, and gel substances, sometimes referred to as LAGs. In one embodiment, methods and systems record an XRD profile of a substance that is subsequently normalized with a best-fit regression line that is part of an Independent Atom Model (IAM) triangular approximation. Further, the methods and systems calculate a ratio of the values associated with the XRD profile and the regression line and form an approximation for the associated MIF for the substance. Moreover, the self-normalization aspects of the methods described herein normalize features of the XRD profile in the lower band of momenta that contains significant signal data against features of the XRD profiles in a higher band of momenta that contains significant noise data. Therefore, the methods and systems are significantly more robust with respect to noise and signal discrimination than the conventional High Energy Tip Region Analysis (HETRA) method. In addition, an approximated MIF of water is subtracted from an approximated MIF of a substance under investigation to yield a residual MIF that improves the signal-to-noise ratio. Utilization of the residual MIF improves material classifications, particularly for aqueous mixtures, with increased accurate detection rates and decreased false alarm rates, with little additional consumption of computational resources and expenditure of time.

A technical effect of the methods and systems described herein is to provide the user of a security system with increased detection rates of contraband substances and decreased false alarm rates of non-contraband substances with less computational resources and processing time than conventional methods. In one embodiment, the technical effect of the methods and systems described herein is to significantly improve noise and signal discrimination over conventional methods. This technical effect is at least partially achieved by generating XRD profiles of a plurality of liquid, amorphous substances, and gel substances, including water. Subsequently, the plurality of XRD profiles of the water and the substance are normalized with a best-fit regression line that is part of an Independent Atom Model (IAM) triangular approximation. For each of the water and the substance, a ratio of the values associated with the XRD profiles and the regression lines form approximations for the associated MIFs for the water and the substance. Features of the XRD profiles in the lower band of momenta that contains significant signal data is normalized against features of the XRD profiles in a higher band of momenta that contains significant noise data. The approximated MIF of water is subtracted from the approximated MIF of the substance under investigation to yield a residual MIF that improves the signal-to-noise ratio. This improved ration allow for improved material classifications, particularly for aqueous mixtures, with increased accurate detection rates and decreased false alarm rates, with little additional consumption of computation resources and expenditure of time.

At least one embodiment is described below in reference to its application in connection with and operation of a security system for monitoring, alarming, and notification. However, it should be apparent to those skilled in the art that the embodiments described herein are likewise applicable to any suitable system requiring security screening of a large number of items of varying substances in a short time frame with little to no false alarms for non-contraband substances and substantially consistent recognition of contraband substances.

At least some of the components of the security systems described herein include at least one processor and a memory, at least one processor input channel, and at least one processor output channel. As used herein, the term "processor" is not limited to integrated circuits referred to in the art as a computer, but broadly refers to a microcontroller, a microcomputer, a programmable logic controller (PLC), an application specific integrated circuit, and other programmable circuits, and these terms are used interchangeably herein. In the embodiments described herein, memory may include, without limitation, a computer-readable medium, such as a random access memory (RAM), and a computer-readable non-volatile medium, such as flash memory. Alternatively, a floppy disk, a compact disc-read only memory (CD-ROM), a magneto-optical disk (MOD), and/or a digital versatile disc (DVD) may also be used. In the embodiments described herein, additional input channels may include, without limitation, computer peripherals associated with an operator interface such as a mouse and a keyboard. Alternatively, other computer peripherals may also be used that may include, for example, without limitation, a scanner. Additional output channels may include, without limitation, an operator interface monitor.

The processors as described herein process information transmitted from a plurality of electrical and electronic components that may include, but not be limited to, security system screening equipment such as x-ray diffraction screening devices. Such processors may be physically located in, for example, the x-ray diffraction screening devices, desktop computers, laptop computers, PLC cabinets, and distributed control system (DCS) cabinets. RAM and storage devices store and transfer information and instructions to be executed by the processor. RAM and storage devices can also be used to store and provide temporary variables, static (i.e., non-changing) information and instructions, or other intermediate information to the processors during execution of instructions by the processors. Instructions that are executed may include, without limitation, resident security system control commands. The execution of sequences of instructions is not limited to any specific combination of hardware circuitry and software instructions.

FIG. 1 is a schematic view of an exemplary security system 100. Security system 100 includes an x-ray source 102, a primary collimator 104, a secondary collimator 106, and a detector 108. Detector 108 includes a central detector element 120 or a central detector cell for detecting primary radiation. Detector 108 also includes a plurality of detector cells or detector elements 122, 124, 216, 128, 130, 132, 134, and 136 for detecting coherent scatter. Detector 108 includes any suitable number of detector elements, ranging from and including 256 to 1024 detector elements, for example. A container 138 is placed on a support 140 between x-ray source 102 and detector 108. Examples of container 138 include a bag, a box, and an air cargo container. Examples of x-ray source 102 include a polychromatic x-ray tube. Container 138 includes a liquid, amorphous substances, and gel substances 142 carried in hold-baggage and checkpoint containers. Examples of liquid substances 142 include, without limitation, water, shampoo, soft drinks, diesel fuel, and alcoholic beverages. As used herein, the term "water" refers to liquid water unless otherwise indicated. Examples of amorphous substances 142 include, without limitation, glass and pitch. Examples of gel substances 142 include, without limitation, hair gel, toothpaste, and sun cream. Examples of support 140 include, without limitation, a table and a conveyor belt. An example of detector 108 includes, without limitation, a segmented detector fabricated from germanium.

X-ray source 102 emits x-rays in an energy range that is dependent on a voltage applied by a power source to x-ray source 102. Using primary collimator 104, a primary beam 144, such as a pencil beam, is formed from the x-rays generated. Primary beam 144 passes through container 138 arranged on support 140 to generate scattered radiation, such as a plurality of scattered rays 146, 148, and 150. A detector 108 is arranged underneath support 140 and is configured to measure an intensity of primary beam 144 and photon energy of the scattered radiation. Detector 108 measures the x-rays in an energy-sensitive manner by outputting a plurality of electrical output signals linearly dependent on a plurality of energies of x-ray quanta detected from within primary beam 144 and the scattered radiation.

Detector elements 120, 122, 124, 126, 128, 130, 132, 134, and 136 are geometrically arranged so that a scatter angle or, alternatively, an incident angle of the scatter radiation detected by each detector element 120, 122, 124, 126, 128, 130, 132, 134, and 136 is constant. For example, an incident angle 152 at which scattered ray 146 is incident on detector element 130 is equal to an incident angle 154 at which scattered ray 148 is incident on detector element 134 and incident angle 154 is equal to an incident angle 156 at which scattered ray 150 is incident on detector element 136. As another example, scattered ray 146 is parallel to scattered rays 148 and 150. Central detector element 120 detects and measures an intensity of primary beam 144 after primary beam 144 passes through container 138. Detector elements 122, 124, 126, 128, 130, 132, 134, and 136 separately detect and measure an energy of scattered radiation received from container 138 after primary beam 144 irradiates container 138.

Secondary collimator 106 is located between support 140 and detector 108. Secondary collimator 106 includes a number of collimator elements (not shown), such as sheets, slits, or laminations, to ensure that the rays of scatter radiation arriving at detector 108 have constant scatter angles with respect to primary beam 144 and that a position of detector 108 permits a depth in container 138 at which the scatter radiation originated to be determined. The number of collimator elements provided is equal to or, alternatively, greater than a number of detector elements 120, 122, 124, 126, 128, 130, 132, 134, and 136. The collimator elements are arranged such that the scattered radiation between neighboring collimator elements is incident on one of the detector elements 122, 124, 126, 128, 130, 132, 134, and 136. The collimator elements are made of a radiation-absorbing material, such as, a copper alloy or a silver alloy. In one embodiment employing a fan-beam geometry, a plurality of origination points, within container 138, of the scatter radiation are detected by detector elements 122, 124, 126, and 128, that are aligned in a first direction and detector elements 130, 132, 134, and 136 that are aligned in a second direction opposite to and parallel to the first direction. Examples of the constant scatter angle values include values ranging from 0.1 degrees for a high-energy device, such as an x-ray tube radiating x-ray photons having an energy of 1 megaelectron-volts (MeV) to four degrees for low-energy systems, such as an x-ray tube radiating x-ray photons having an energy of 150 kiloelectron-volts (keV). Detector 108 detects the scattered radiation to generate a plurality of electrical output signals such as, without limitation, electrical pulses having a measurable voltage amplitude and a measurable duration. In an alternative embodiment, system 100 does not include primary and secondary collimators 104 and 106.

Figure 2:
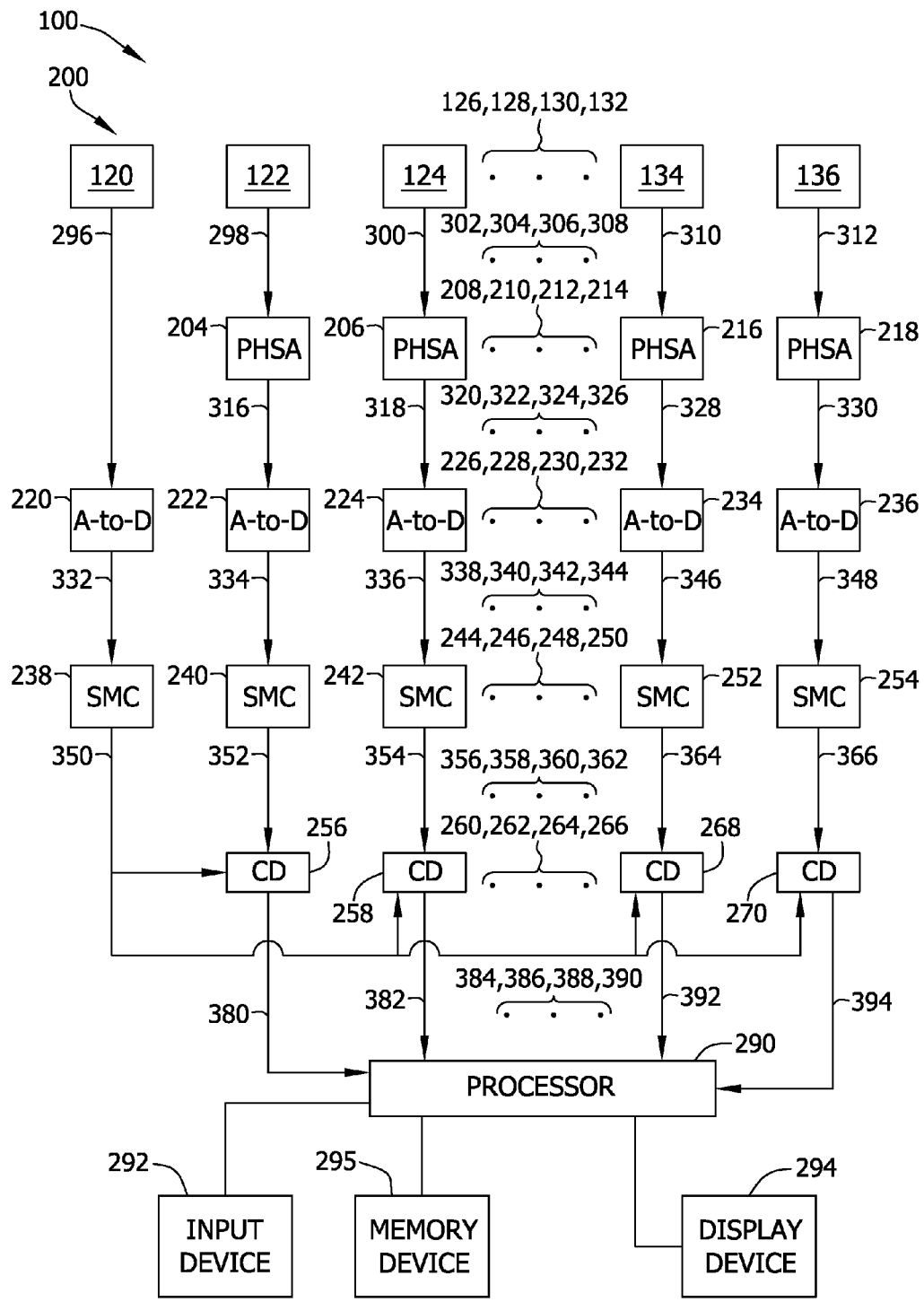

FIG. 2 is a schematic view of an exemplary substance determination system 200 that may be used with security system 100. In the exemplary embodiment, substance determination system 200 facilitates determining an atomic number of substance 142 (shown in FIG. 1), thereby facilitating identification of substance 142. Also, in the exemplary embodiment, system 200 includes a plurality of pulse-height shaper amplifiers (PHSAs) 204, 206, 208, 210, 212, 214, 216, and 218 operatively coupled to detector elements 122, 124, 126, 128, 130, 132, 134, and 136, respectively. PHSAs 204 through 218 are configured to amplify electrical output signals (as described above and discussed further below) received from detector elements 122 through 136, respectively, with predetermined gain values.

System 200 further includes a plurality of analog-to-digital (A-to-D) converters 220, 222, 224, 226, 228, 230, 232, 234, and 236. A-to-D converter 220 is operatively coupled to detector element 120. A-to-D converters 222 through 236 are operatively coupled to PHSAs 204 through 218, respectively. A-to-D converter 220 is configured to convert unamplified amplitude values to discrete, digital output signals with amplitude values representative of x-ray quanta values, for example, photonic intensity values of photons interacting with detector element 120. A-to-D converters 222 through 236 are configured to convert an amplified analog output signal transmitted from PHSAs 204 through 218 to discrete, digital output signals with amplitude values representative of x-ray quanta values, for example, photonic energy values for A-to-D converters 222 through 236 of photons interacting with detector elements 122 through 136.

System 200 also includes a plurality of spectrum memory circuits (SMCs) 238, 240, 242, 244, 246, 248, 250, 252, and 254 operatively coupled to A-to-D converters 220 through 236, respectively. SMCs 238 through 254 include an additive device (not shown) that sums a number of discrete pulses representative of x-ray quanta detected by respective detector elements 120 through 136 and received from respective A-to-D converters 220 through 236, respectively. SMCs 238 through 254 also include a memory device (not shown) that stores the number of discrete pulses. Further, SMCs 238 through 254 are configured to generate signals representative of a number of x-ray photons having a predetermined range of energies for use as described further below.

System 200 further includes a plurality of correction devices (CDs) 256, 258, 260, 262, 264, 266, 268, and 270 operatively coupled to SMCs 240 through 254, respectively, and each of CDs 256 through 270 is operatively coupled to SMC 238. CDs 256 through 270 are configured to determine corrective values that are applied to the signals representative of a number of x-ray photons having a predetermined range of energies transmitted from each respective SMC 240 through 254. Such signals transmitted from each respective SMC 240 through 254 are compared to signals transmitted from SMC 238. Signals transmitted from SMC 238 are representative of a number of x-ray photons having a predetermined range of intensities, since SMC 238 is operatively coupled to central detector element 120 as described above. Each CD 256 through 270 generates a correction output signal that represents a ratio of a number of x-rays photons having a range of energies within x-ray quanta received by detector elements 122 through 136 as compared to a number of x-rays photons having a range of intensities within x-ray quanta received by central detector element 120. Each of CDs 256 through 270 includes, for example, and without limitation, a divider circuit (not shown).

System 200 also includes a processor 290 operatively coupled to each CD 256 through 270. Processor 290 is operatively coupled to an input device 292, a display device 294, and a memory device 295. As used herein, the term processor is not limited to integrated circuits referred to in the art as a processor, but broadly refers to, without limitation, a computer, a microcontroller, a microcomputer, a programmable logic controller (PLC), an application specific integrated circuit, and any other programmable circuit. Processor 290 may also be configured to execute instructions stored in firmware. Input device 292 may include a device, such as, without limitation, a floppy disk drive or CD-ROM drive, for reading data including the methods for determining an atomic number of a substance from a computer-readable medium, such as, without limitation, a floppy disk, a compact disc-read only memory (CD-ROM), a magneto-optical disk (MOD), or a digital versatile disc (DVD). Examples of input device 292 include, without limitation, a mouse and a keyboard. Examples of display device 294 include, without limitation, a liquid crystal display (LCD) and a cathode ray tube (CRT). Examples of memory device 295 include, without limitation, a random access memory (RAM) and a read-only memory (ROM). Similarly, and as described above, the memory device of each of SMCs 238 through 254 includes, for example, without limitation, a RAM or a ROM.

In operation, central detector element 120 detects and measures an intensity of primary beam 144 after primary beam 144 passes through container 138. Detector elements 122, 124, 126, 128, 130, 132, 134, and 136 separately detect and measure an energy of scattered radiation received from container 138 after primary beam 144 irradiates container 138. Central detector element 120 generates an electrical output signal 296 by detecting primary beam 144 and detector elements 122, 124, 126, 128, 130, 132, 134, and 136 generate a plurality of electrical output signals 298, 200, 302, 304, 306, 308, 310, and 312, respectively, by detecting scattered radiation. For example, detector element 122 generates electrical output signal 298 for each scattered x-ray photon incident on detector element 122.

In the exemplary embodiment, signals 296 through 312 are electrical output signals such as, without limitation, electrical pulses having a measurable voltage amplitude and a measurable duration. In general, such amplitude of an electrical output signal output from a detector element is proportional to one of an integrated intensity or an integrated energy of an x-ray quantum that is detected by the detector element to generate the electrical output signal. For example, an amplitude of electrical output signal 296 is proportional to an integrated intensity of an x-ray quantum in primary beam 144 detected by detector element 120. Further, for example, an amplitude of electrical output signal 298 is proportional to an integrated energy of an x-ray quantum within scattered radiation that is detected by detector element 122. Signals 300 through 312 as generated and transmitted by detectors 122 through 136 are similar in nature, if not amplitude and duration, to signals 298.

Also, in operation, each PHSA 204 through 218 receives and amplifies respective electrical output signals 298 through 312 as transmitted by respective detector elements 122 through 136. PHSAs 204 through 218 have a gain value determined by processor 290. For example, PHSA 204 receives and amplifies electrical output signal 298 and generates amplified output signal 316. Therefore, each PHSA 204 through 218 generates and transmits a respective amplified output signal 316, 318, 320, 322, 324, 326, 328, and 330 by amplifying respective electrical output signals 298 through 312 as transmitted by respective detector elements 122 through 136.

Further, in operation, A-to-D converter 220 receives, and converts from an analog form to a digital form, respective unamplified output signals 296 as transmitted from detector element 120 to generate a discrete, digital output signal 332. Moreover, each A-to-D converter 222 through 236 receives, and converts from an analog form to a digital form, respective amplified output signals 316 through 330 as transmitted from respective PHSAs 204 through 218. For example, A-to-D converter 222 receives and converts amplified output signal 316 from an analog form to a digital format to generate a plurality of discrete, digital output signals 334. Therefore, each A-to-D converter 222 through 236 generates and transmits a respective plurality of discrete, digital output signals 334, 336, 338, 340, 342, 344, 346, and 348 by digitizing respective amplified output signals 316 through 330 as transmitted by respective PHSAs 204 through 218.

In general, in the exemplary embodiment, a discrete, digital value of a digital output signal as generated by an analog-to-digital converter represents one of an amplitude of energy of a pulsed, amplified output signal or an amplitude of intensity, of a pulsed, unamplified output signal. Each pulse is generated by an x-ray quantum, such as an x-ray photon. For example, a digital value of digital output signal 332 generated and transmitted by A-to-D converter 220 is representative of a pulse amplitude value associated with unamplified output signal 296. Also, for example, a digital value of digital output signal 334 generated and transmitted by A-to-D converter 222 is representative of a pulse amplitude value associated with amplified output signal 316.

Moreover, in operation, each SMC 238 through 254 receives respective digital output signals 332 through 348 as transmitted from respective A-to-D converters 220 through 236. In general, the adder device of a spectrum memory circuit sums a number of discrete pulses received from a digital output signal, such discrete pulses representative of one of an amplitude of energy or an amplitude of intensity, of those photons detected by the respective detector element. Also, in general, the memory device of each spectrum memory circuit stores the values determined by the associated adders.

For example, when A-to-D converter 220 converts a pulse of amplified output signal 296 into digital output signal 332, such signal 332 having a value representative of an amplitude of amplified output signal 296, an adder within SMC 238 increments, by one, a value within the memory device of SMC 238. Accordingly, at an end of an x-ray examination of substance 142, the memory device within SMC 238 stores a number of x-ray quanta detected by detector element 120 with a predetermined amplitude of intensity of such detected photons. Therefore, SMC 238 generates and transmits a respective discrete output signal 350 representative of a number of x-ray quanta detected by respective detector elements 120 with a predetermined amplitude of intensity of such detected photons.

Moreover, for example, when A-to-D converter 222 converts a pulse of amplified output signal 316 into digital output signal 334, such signal 334 having a value representative of an amplitude of amplified output signal 316, an adder within SMC 240 increments, by one, a value within the memory device of SMC 240. Accordingly, at an end of an x-ray examination of substance 142, the memory device within SMC 240 stores a number of x-ray quanta detected by detector element 122 with a predetermined amplitude of energy of such detected photons. Therefore, each SMC 240 through 254 generates and transmits a respective discrete output signal 352, 352, 354, 356, 358, 360, 362, 364, and 366 representative of a number of x-ray quanta detected by respective detector elements 122 through 136 with a predetermined amplitude of energy of such detected photons.

Also, in operation, each CD 256 through 270 receives respective digital output signals 352 through 366 as transmitted from respective SMCs 240 through 254. Further, each CD 256 through 270 receives digital output signal 350 as transmitted from SMC 238. In general, in the exemplary embodiment, a correction device receives a first signal representative of a number of x-ray quanta within the predetermined range of energies stored within a memory device of a first spectrum memory circuit, and receives a second signal representative of a number of x-ray quanta within the predetermined range of intensities stored within a memory device of a second spectrum memory circuit, and divides the first number by the second number, thereby generating a correction output signal that represents a range of energies, or an energy spectrum, associated with the x-ray quanta received by a detector element. For example, CD 256 receives digital output signal 352 from associated SMC 240 and also receives digital output signal 350 from associated SMC 238. CD divides signal 352 by signal 350 and generates a correction output signal 380 representing an energy spectrum associated with the x-ray quanta detected by detector element 122. Therefore, each CD 256 through 270 generates and transmits a respective correction output signal 380, 382, 384, 386, 388, 390, 392, and 394 representative of an energy spectrum associated with x-ray quanta received by respective detector elements 122 through 136.

Further, in operation, processor 290 receives correction output signals 380 through 394 to generate values for a momentum transfer variable x that is measured in inverse nanometers ($nm^{-1}$). The terms momentum and, in plural, momenta, are typically used to indicate a momentum transfer value, that is, the amount of momentum transferred from a first particle to a second particle and/or the amount of momentum transferred from a first wave to a second wave, or, as used herein, an increase in a photonic momentum as a result of an interaction of a portion of substance 142 (shown in FIG. 1) with a scattered x-ray.

Momentum transfer variable x is defined within a range of energies E of x-ray quanta, that is an energy spectrum r(E), of the scattered radiation detected by detector 108. Processor 290 generates the momentum transfer variable x by applying the equation:

$$x=(E/hc)*\sin(\theta/2)=(1/\lambda)*\sin(\theta/2), \quad \text{Eq. (1)}$$

wherein x represents the momentum transfer variable, E represents the energy of x-ray quanta of the scattered radiation detected by detector 108, h represents Planck's constant, c represents the speed of light, θ represents constant scatter angles of x-ray quanta of the scattered radiation detected by detector 108, and λ represents an x-ray wavelength and is equivalent to (hc/E). Processor 290 relates the energy E to the momentum transfer variable x by Eq. (1). Mechanical dimensions of secondary collimator 106 define the scatter angle θ and restricts the scatter radiation that does not have the angle θ. Processor 290 receives the scatter angle θ from a user via input device 292.

Figure 3:
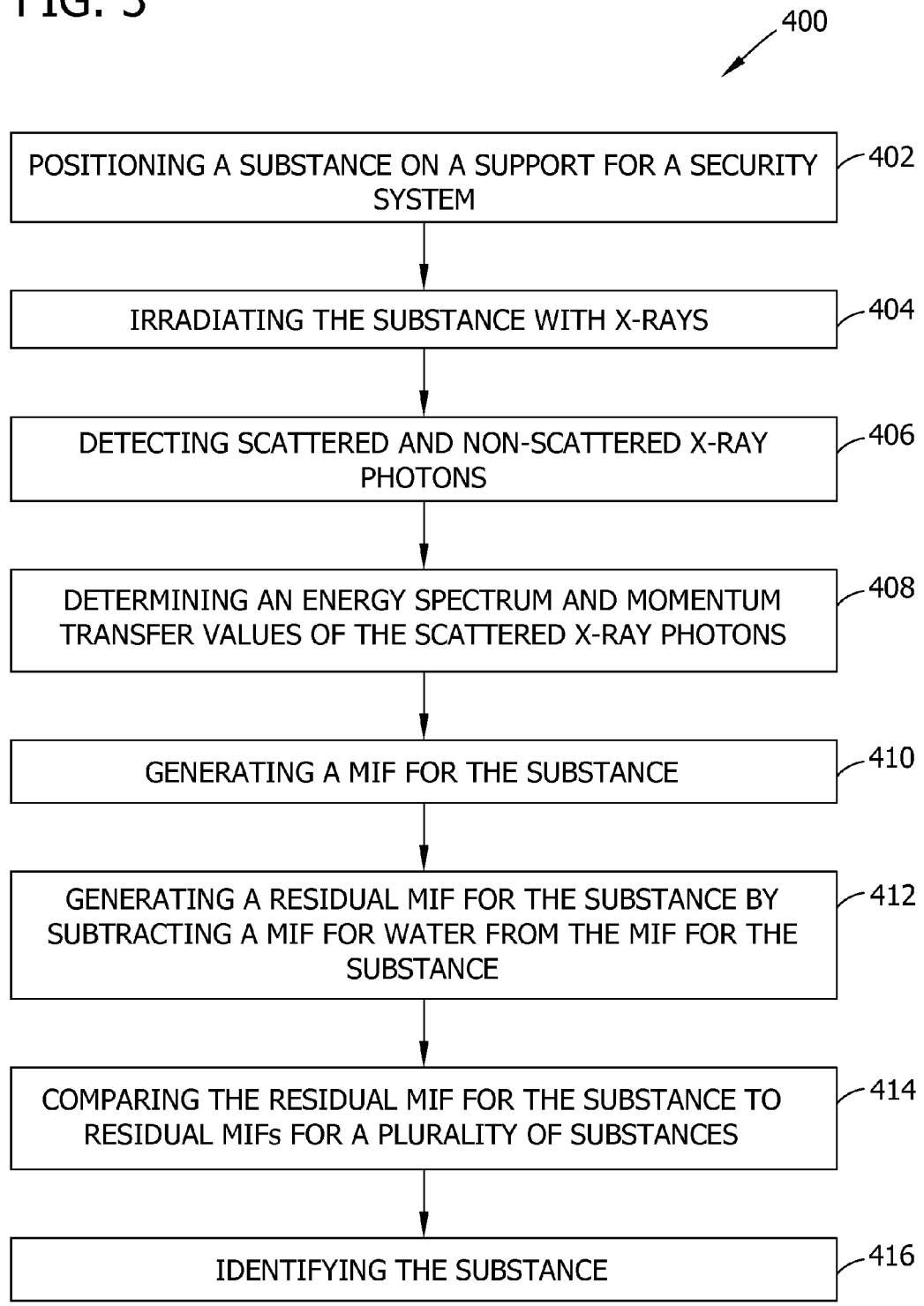

FIG. 3 is a flow chart of an exemplary method 400 of screening a substance using security system 100 (shown in FIG. 1). Method 400 is performed from the perspective of an operator of security system 100. In the exemplary embodiment, method 400 includes positioned 402 substance 142, within container 138, within security system 100 on support 140 (all shown in FIG. 1). Substance 142 is irradiated 404 with primary beam 144 of x-rays generated by x-ray source 102 (both shown in FIG. 1). Detector elements 120 through 136 detect 406 scattered and non-scattered x-ray photons. Substance determination system 200 determines 408 an energy spectrum and momentum transfer values of the scattered x-ray photons. System 200 then generates 410 a MIF for substance 142 stored within processor 290 and/or memory device 295. System 200 also compares and/or subtracts a MIF substantially associated with water, such MIF for water stored within processor 290 and/or memory device 295, with/from the MIF for substance 142, thereby generating 412 a residual MIF for substance 142. Such residual MIF for substance 142 is compared 414 to a plurality of residual MIFs stored within processor 290 and/or memory device 295. The operator of system 200 is provided 416 with an identification of substance 142 via display device 294. Moreover, display device 294 may inform the operator of system 200 with a contraband substance and/or dangerous substance warning and/or alert, depending on the nature and/or composition of substance 142.

Figure 4:
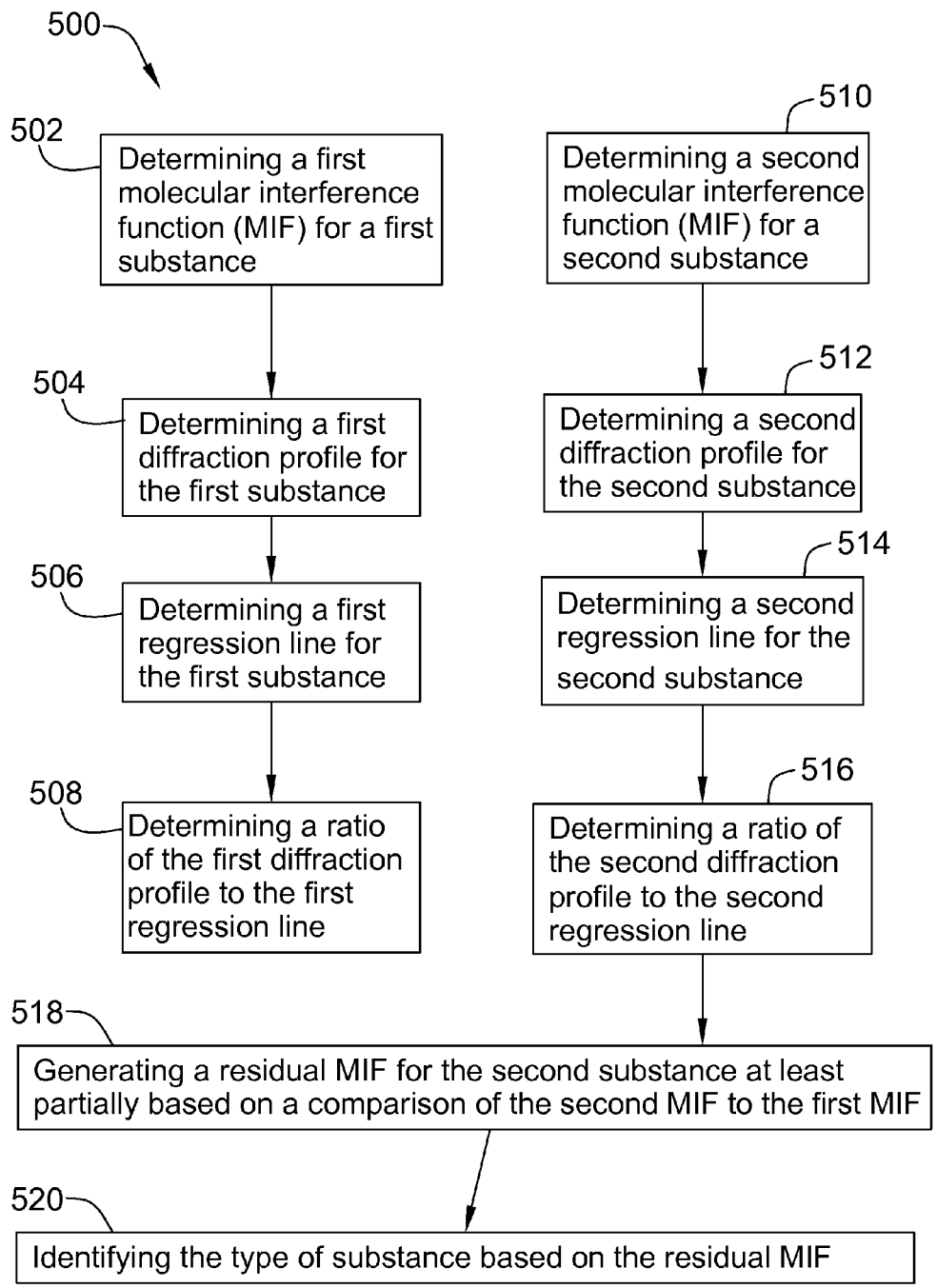

FIG. 4 is a flow chart of an exemplary method 500 of identifying a substance using substance determination system 200. Method 500 is performed from the perspective of a technician programming processor 290 to implement at least a portion of system 200 therein. Method 500 as described herein enables portions of method 400 (shown in FIG. 3) including method steps 408 through 416. In the exemplary embodiment, the first substance is water and the second substance includes one of a liquid substance, an amorphous substance, and a gel substance, all as defined above. Method 500 includes determining 502 a first MIF for water that includes determining 504 a first diffraction profile for water, determining 506 a first regression line for water at least partially based on the first diffraction profile, and determining 508 a ratio of the diffraction profile to the first regression line. Method steps 502 through 508 are described further below.

A second MIF is determined 510 for the second substance that includes determining 512 a second diffraction profile for the second substance, determining 514 a second regression line for the second substance at least partially based on the second diffraction profile, and determining 516 a ratio of the second diffraction profile to the second regression line. Method steps 510 through 516 are described further below.

Further, in the exemplary embodiment, method 500 includes generating 518 a residual MIF for the second substance at least partially based on a comparison of the second MIF to first MIF. The substance is then identified 520 based on the residual MIF. Method steps 518 and 520 are described further below.

Figure 5:
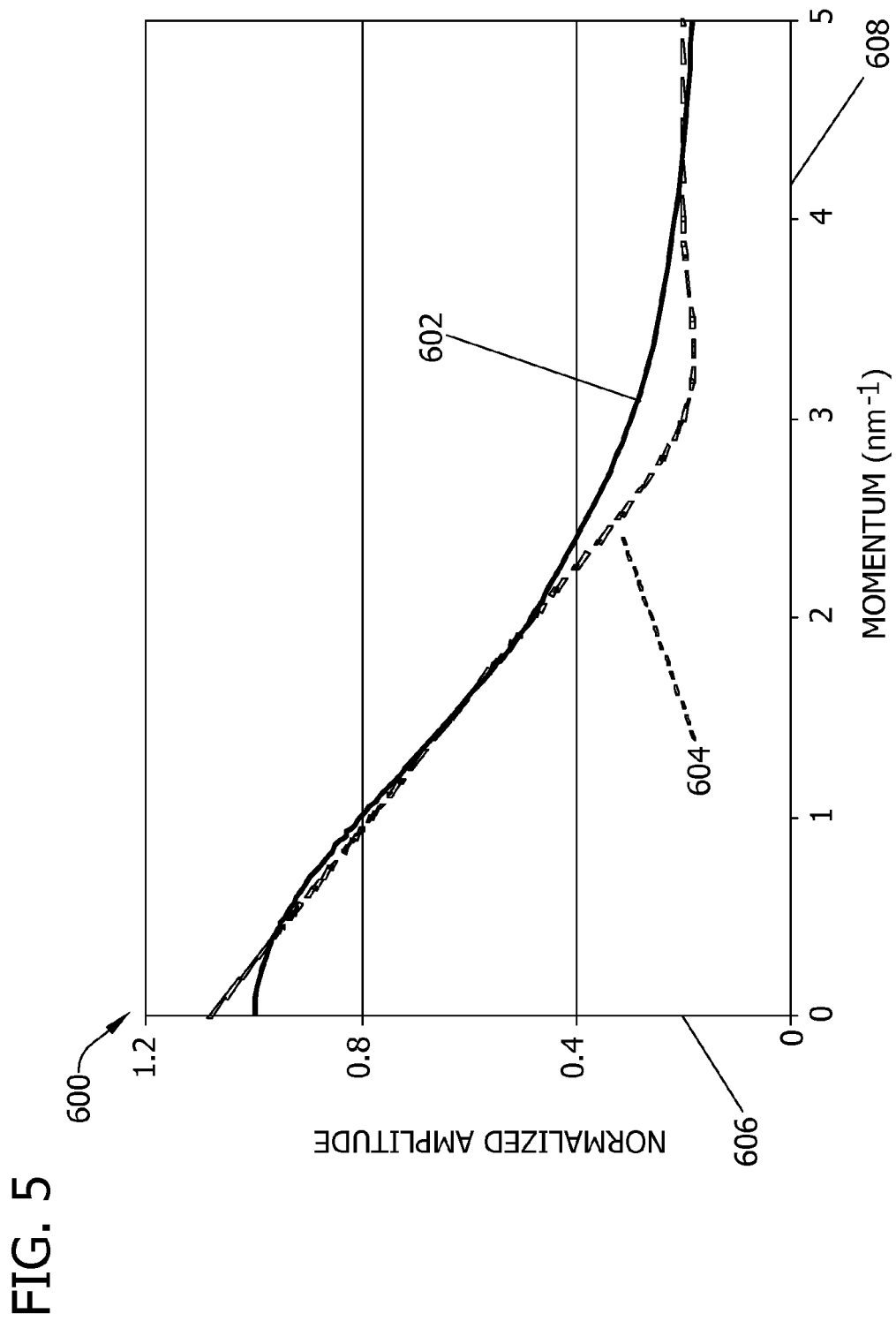

FIG. 5 is a graphical view 600 of a comparison of a scatter function curve 602 for nitrogen calculated using an Independent Atom Model (IAM) and a scatter function curve 604 using a triangular IAM approximation for nitrogen using security system 100 (shown in FIG. 1). Determining such triangular IAM approximation facilitates performing method 500 including determining 502 a first MIF for a first substance, or water that includes determining 504 a first diffraction profile for water. Also, determining such triangular IAM approximation facilitates determining 510 a second MIF for a second substance that includes determining 512 a second diffraction profile for the second substance. While curves 602 and 604 represent data associated with nitrogen, other elements with relatively low atomic numbers having some importance for security screening show similar agreement with the triangular IAM approximation for nitrogen.

Curve 604 for nitrogen is defined using methods as described herein. Graphical view 600 includes an ordinate (y-axis) 606 that represents a normalized signal amplitude in unitless values, such values at least partially represent a number of photons detected as a function of scattered x-rays within the nitrogen. The normalization process is described further below. Graphical view 600 also includes an abscissa (x-axis) 608 that represents a momentum of the detected photons in units of inverse nanometers, or $nm^{-1}$. Both y-axis 606 and x-axis 608 define an origin at 0, 0.

In the exemplary embodiment, when a decay in detected photons drives curve 602 below a certain proportion, that is, when y is within a range of approximately 10% to approximately 20% of the maximum height of curve 602 at x=0, curve 602 approximates a substantially constant, horizontal line. Therefore, at x=0, curve 602 indicates that y has a value of approximately 1.0, and at approximately x=4, curve 602 is relatively flat with a value of y at approximately 0.2. Further, curve 604 approximates a horizontal line at a similar value of x. As shown in FIG. 5, curve 604 substantially tracks with curve 602, thereby indicating a close agreement between IAM curve 602 and IAM approximation curve 604. The agreement extends to momentum values less than or equal to approximately 5 $nm^{-1}$. While curves 602 and 604 represent data associated with nitrogen, other elements with relatively low atomic numbers having some importance for security screening show similar agreement with the triangular IAM approximation for nitrogen.

Graphical view 600 shows that a triangular IAM approximation may be a good approximation of at least a portion of an IAM curve, therefore method 500 may be preformed with less computational resources and processing time than conventional methods.

Figure 6:
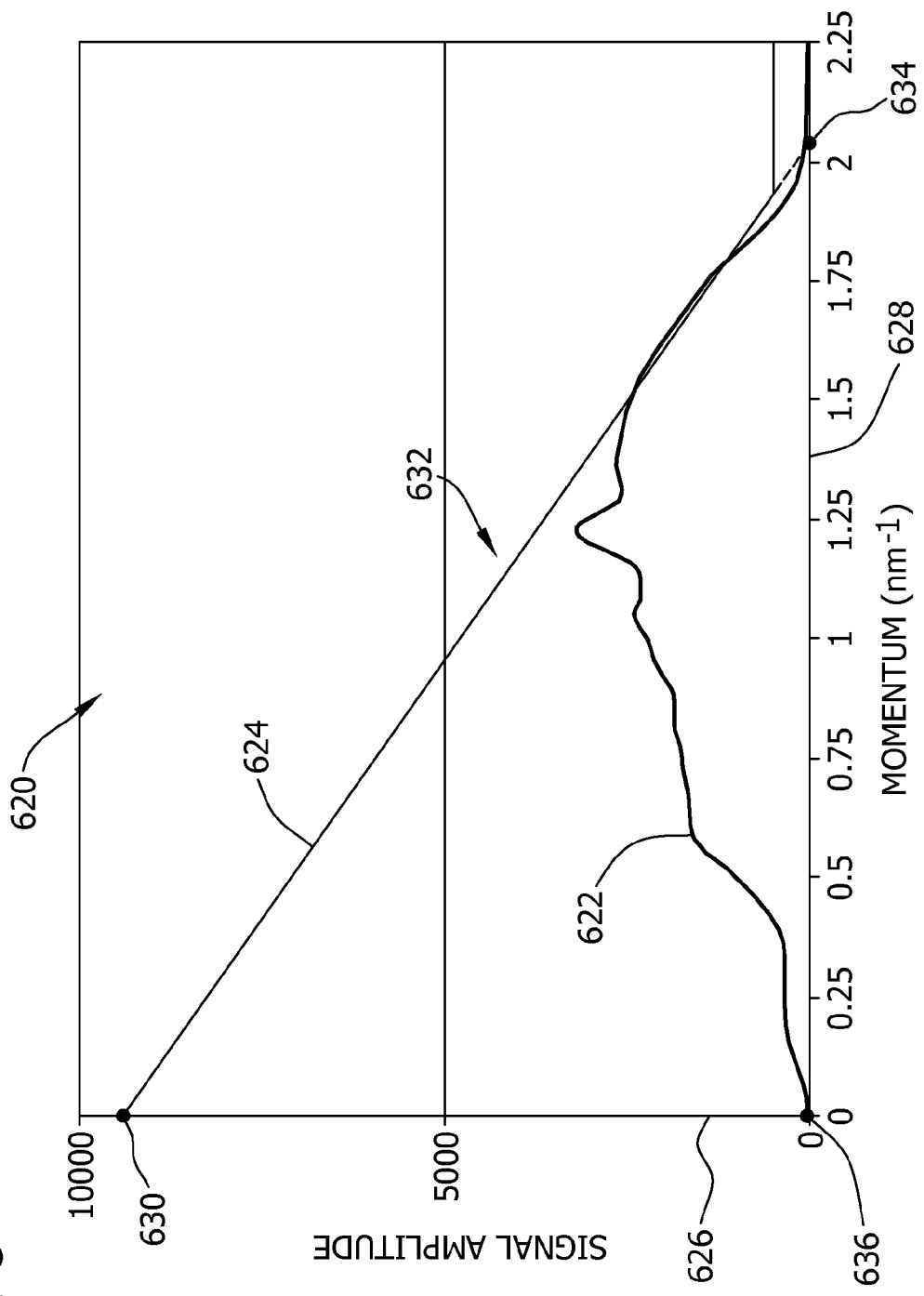

FIG. 6 is a graphical view 620 of an x-ray diffraction (XRD) profile curve 622 of water generated by security system 100 (shown in FIG. 1) and a best-fit normalized regression line 624 derived from XRD profile curve 622. Graphical view 620 shows an example of determining 502 a first MIF for water that includes determining 504 a first diffraction profile for water and determining 506 a first regression line for water at least partially based on the first diffraction profile (all shown in FIG. 4). Water was chosen as it is a liquid material that is by far the most common solvent used for liquids, amorphous substances, and gels carried in hold-baggage and checkpoint containers. Also, the water molecule is the smallest of all liquids at room temperature.

Graphical view 620 includes an ordinate (y-axis) 626 that represents a signal amplitude in units of number of photons detected as a function of scattered x-rays within the water. Graphical view 620 also includes an abscissa (x-axis) 628 that represents a momentum of the detected photons in units of inverse nanometers, or $nm^{-1}$. Both y-axis 626 and x-axis 628 define an origin at 0, 0.

Curve 622 indicates that at low momentum values, that is, at values less than approximately 1.5 $nm^{-1}$, a molecular contribution to the number of scattered x-rays, and the resultant photons and photon noise, is too large to be ignored and the IAM is not well described in this region. Therefore, higher values of momentum, that is, values greater than 1.5 $nm^{-1}$, indicate a better relationship with the IAM.

Moreover, photon values at lowest momentums, i.e., at momentums less than approximately 0.5 $nm^{-1}$, are related to an isothermal compressibility of water and such compressibility of water is typically smaller than compressabilities for most other room-temperature liquids. This property of water affects approximating a MIF for water in that momentum range.

MIFs are a function of momentum transfer variable x as defined in Eq. (1) above. MIFs are further defined as a Fourier pair with a radial distribution function, that is, g(r), such that a g(r) may be derived once the associated MIF has been determined. Radial distribution functions are associated with electric charge distributions per unit volume within a liquid substance with respect to an arbitrary origin. Fourier pairs define two quantities that use Fourier transforms of each other, for example, position and momentum.

For example, a radial distribution function describes a probability per unit volume of a substance S (not shown) of finding a particle (not shown) of type A at a radial distance $R_A$ (not shown) from an origin of coordinates, at which another particle A (not shown) is located. Moreover, if substance S also includes particles of type B (not shown), a second radial distribution function describes a probability per unit volume of substance S of finding a particle of type B at a radial distance $R_B$ (not shown) from the origin of coordinates, at which another particle B (not shown) is located. Furthermore, a third radial distribution function similarly defines a probability per unit volume of substance S of finding particles of either type A or type B. A type A particle and a type B particle may define a relationship that includes a radial distance therebetween. For example, a type A particle defines a relationship with a type B particle that includes a radial distance $R_{AB}$ (not shown) from the origin. An overall radial distribution function of substance S is a sum of the three component radial distribution functions.

Similarly, in the example, due to a linear relationship between the Fourier pairs that define MIFs and radial distribution functions, the overall MIF is also the sum of three component functions. For a low concentration solution of solute B in solvent A, the overall MIF is dominated by two functions that define probabilities associated with a type A-to-type A particle distribution and a type A-to-type B particle distribution, with a function that defines a probability of a type B-to-type B particle distribution that induces a minor influence. Therefore, a MIF for an aqueous mixture (assuming no chemical reaction takes place when the mixture is formed) is a sum of a water MIF and a MIF describing the spatial organization of solute particles relative to the water molecules.

In the exemplary embodiment, XRD profile curve 622 is plotted between a lower limit of approximately 1.6 $nm^{-1}$ and an upper limit of approximately 2.25 $nm^{-1}$ with best-fit regression line 624 fitted thereon. Line 624 is linearly extended from 1.5 $nm^{-1}$ to intersect y-axis 626 at a first point 630 of a triangle 632. A second point 634 of triangle 632 is defined at an intersection of line 624 with x-axis 628. A third point 636 is defined at the origin of y-axis 626 and x-axis 628, representing the apex of the triangle. When the triangular line falls below a certain fraction of its apex height, it converts to a horizontal line (constant).

Triangle 632 represents a triangular approximation of an IAM of water. The approximation is relatively free from systematic errors as the approximation implements a self-normalization procedure in which features of XRD profile curve 622 lying in a lower range of momentum values defined on x-axis 628, i.e., a lower band of momenta of approximately 0.5 nm$^{-1}$ to approximately 1.5 nm$^{-1}$, are normalized against features in a higher band of momenta of approximately 1.6 nm$^{-1}$ to approximately 2.25 nm$^{-1}$. Moreover, the approximation uses a region of XRD profile 622 at moderate momenta where most of the signal is located and is thus much more noise-robust than conventional HETRA methods. Furthermore, the IAM approximation is based on two assumptions. The first assumption is that the IAM functions of low-atomic number atoms are triangular. The second assumption is that for liquids, amorphous substances, and gel substances, the deviations from unity of a subsequent approximate MIF (discussed below) are small for momenta values beyond that corresponding to the principal peak position, for example, approximately 1.25 nm$^{-1}$ to approximately 1.5 nm$^{-1}$, as shown in FIG. 6.

Figure 7:
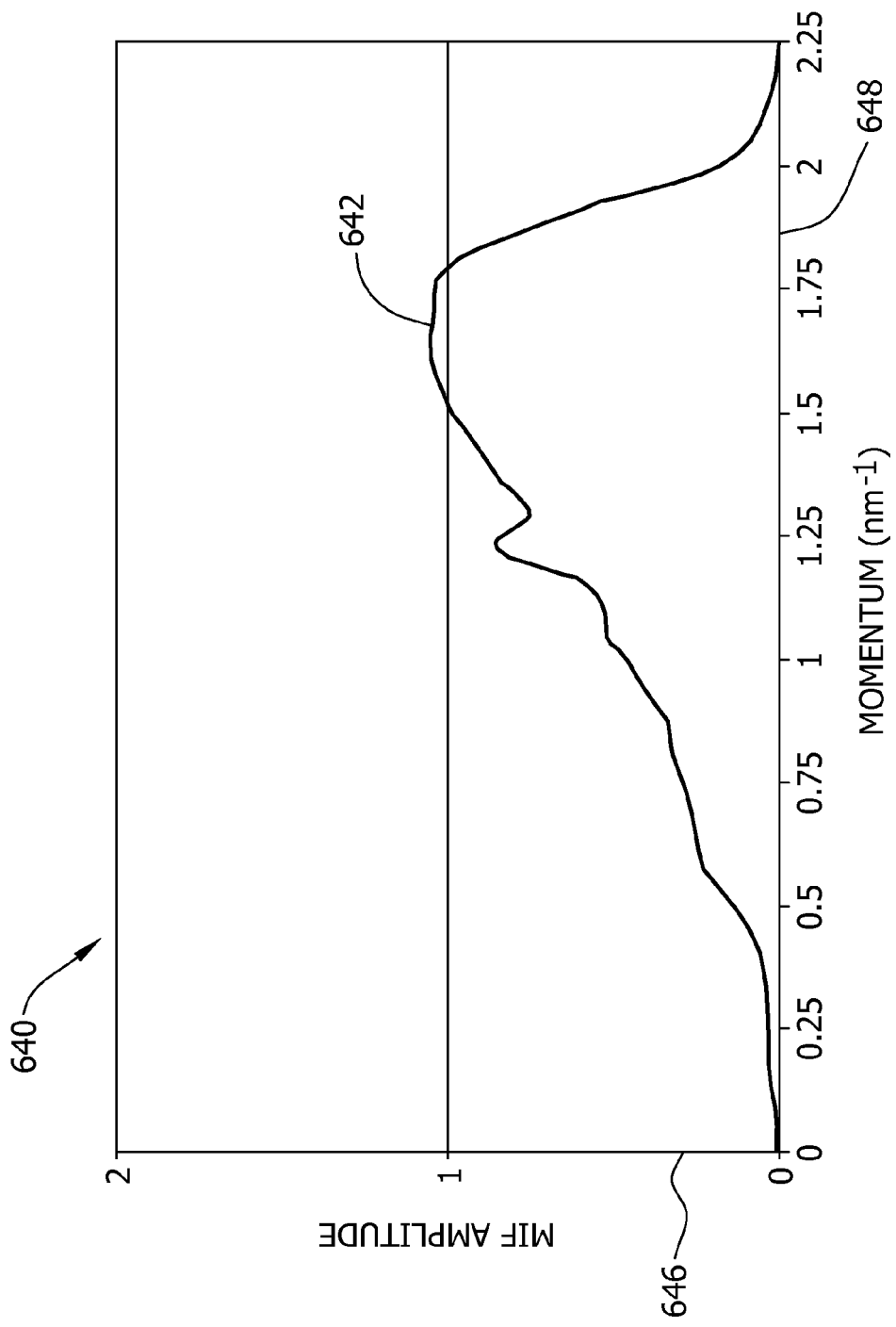

FIG. 7 is a graphical view 640 of an approximated MIF curve 642 for water using XRD profile curve 622 and normalized regression line 624 (both shown in FIG. 6). Graphical view 640 shows an example of determining 502 a first MIF for water that includes determining 508 (both shown in FIG. 4) a ratio of XRD profile curve 622 to regression line 624 (both shown in FIG. 6).

Graphical view 640 includes an ordinate (y-axis) 646 that represents a normalized MIF amplitude in unitless values that at least partially represent a number of photons detected as a function of scattered x-rays within the water. Graphical view 640 also includes an abscissa (x-axis) 648 that represents a momentum of the detected photons in units of inverse nanometers, or nm$^{-1}$. Both y-axis 646 and x-axis 648 define an origin at 0, 0.

In the exemplary embodiment, approximated MIF curve 642 is determined by calculating a ratio of measured XRD profile curve 622 to normalized regression line 624 for each value of momentum, that is, by dividing curve 622 by line 624. As discussed above, photon values at lowest momentums, i.e., at momentums less than approximately 0.5 nm$^{-1}$, are related to an isothermal compressibility of water and such compressibility of water is typically smaller than compressabilities for most other room-temperature liquids. This property of water affects approximating MIF curve 642 for water in that momentum range. Therefore, MIF curve 642 represents a reasonable approximation of a MIF for water in the momentum range of approximately 0.6 nm$^{-1}$ to approximately 2.1 nm$^{-1}$.

Figure 8:
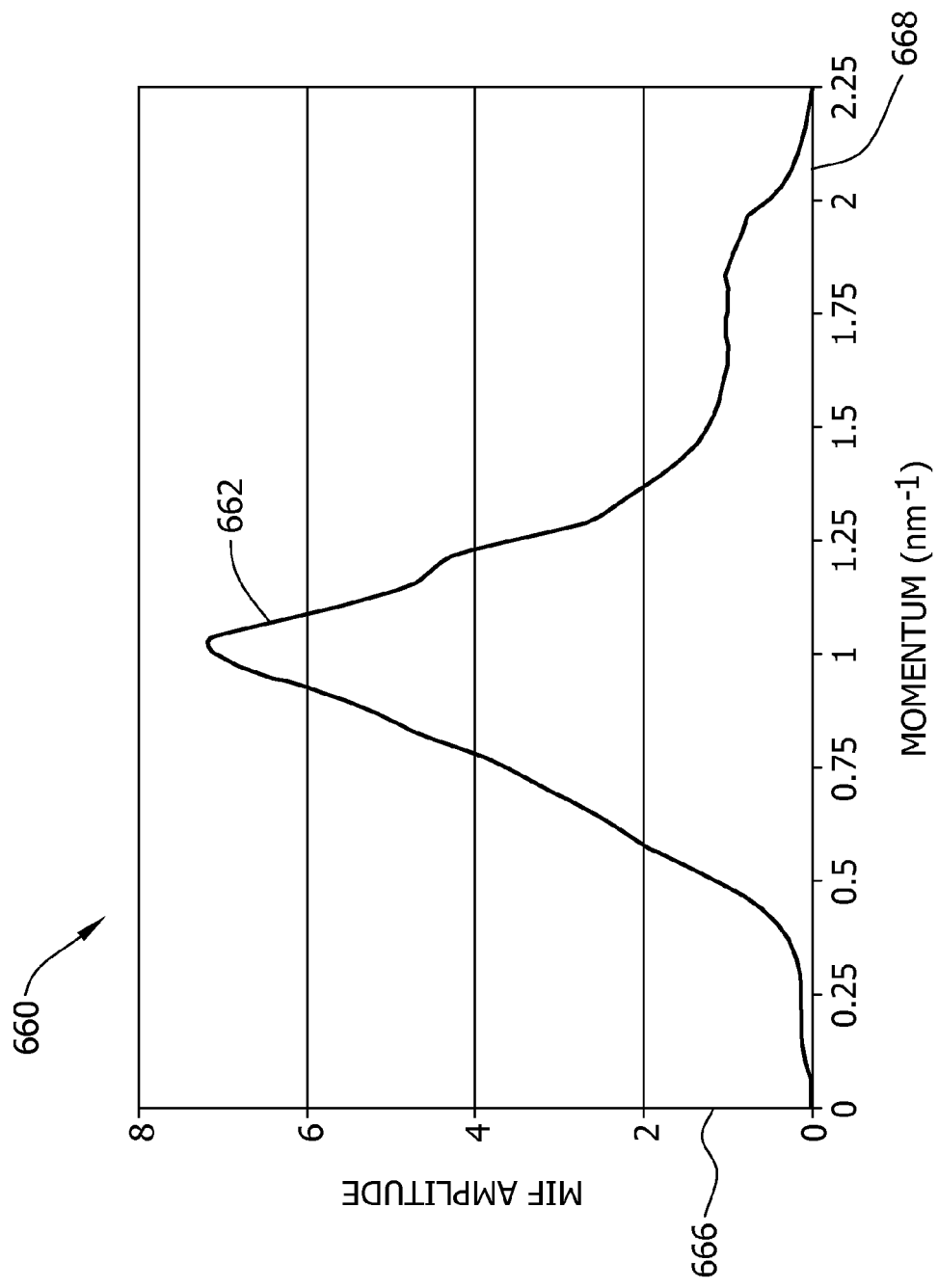

FIG. 8 is a graphical view 660 of an approximated MIF curve 662 for number 2 diesel fuel generated by security system 100 (shown in FIG. 1). Graphical view 640 shows an example of determining 510 a second MIF for the second substance that includes determining 512 a second diffraction profile for the second substance, determining 514 a second regression line for the second substance at least partially based on the second diffraction profile, and determining 516 a ratio of the second diffraction profile to the second regression line (all shown in FIG. 4). In the exemplary embodiment, method steps 512 and 514 are substantially similar to method steps 504 and 506 (both shown in FIG. 4) as performed for water and described above (shown in FIGS. 6 and 7). Therefore, performance of method steps 512 and 514 for number 2 diesel fuel and a diffraction profile and a regression line for number 2 diesel fuel are not discussed or shown. Also, in the exemplary embodiment, in a manner similar to that described above for method step 504 for water (shown in FIG. 5), determining 512 a diffraction profile for number 2 diesel fuel includes determining a triangular IAM approximation for number 2 diesel fuel.

Graphical view 660 includes an ordinate (y-axis) 666 that represents a normalized MIF amplitude in unitless values that at least partially represent a number of photons detected as a function of scattered x-rays within the diesel fuel. Graphical view 660 also includes an abscissa (x-axis) 668 that represents a momentum of the detected photons in units of inverse nanometers, or nm$^{-1}$. Both y-axis 666 and x-axis 668 define an origin at 0, 0.

Diesel fuel is typical of the fuel oils used in ammonium nitrate/fuel oil (ANFO) explosives. In contrast to water MIF curve 642 (shown in FIG. 7), diesel MIF curve 662 displays a higher value at 0.5 nm$^{-1}$ due to diesel fuel being more compressible than water. Moreover, diesel fuel has higher values for a radial distribution function as described above, therefore MIF amplitude values for diesel fuel are typically higher than those for water at similar momentums.

In general, in the exemplary embodiment, a plurality of properties unique to each liquid, amorphous substance, and gel substance are used to identify such liquids and/or materials during security screening processes. For example, and as described above, each liquid/material has well defined compressibility characteristics that at least partially define an associated MIF curve for such liquids/materials. Moreover, in the momentum region that defines a normalized regression line, an area under the regression line is approximately equal to the area under the XRD profile curve, therefore a ratio of an area under the curve to an area under the line is approximately unity for that momentum range. Also, generally, and similar to the liquids and materials described herein, for a gaseous substance having an associated XRD profile normalized to that of an associated triangular IAM function, a ratio of the area under the XRD curve normalized to the area under the regression line would be approximately unity. The ratio is at least partially related to a degree of spatial order within the gaseous substance as a function of the gaseous substance's compressibility characteristics.

The linear regression fit procedure as described above to define a regression line from an XRD curve using a triangular IAM approximation is fast with contemporary computers. Further, limiting computations, for example, without limitation, to a momentum range of approximately 1.6 nm$^{-1}$ to 2.1 nm$^{-1}$ facilitates speed of computations for a wide variety of fluids. Alternatively, any limited range of momenta to which computations are constrained that enables operation of system 100 as described herein is used. Therefore, the triangular IAM fit procedure as described herein is fast, noise-robust, and is relatively free from systematic errors as the triangular IAM fit procedure implements a self-normalization procedure, in which features of the XRD profile lying in one band of momenta (0.5 nm$^{-1}$ to 1.5 nm$^{-1}$) are normalized against features in another band of momenta (1.6 nm$^{-1}$ to 2.1 nm$^{-1}$). Because the triangular IAM fit procedure is noise-robust, the procedure performs a more accurate analysis of liquid identity than HETRA, thereby facilitating lower false-alarm rates and higher detection rates.

Figure 9:
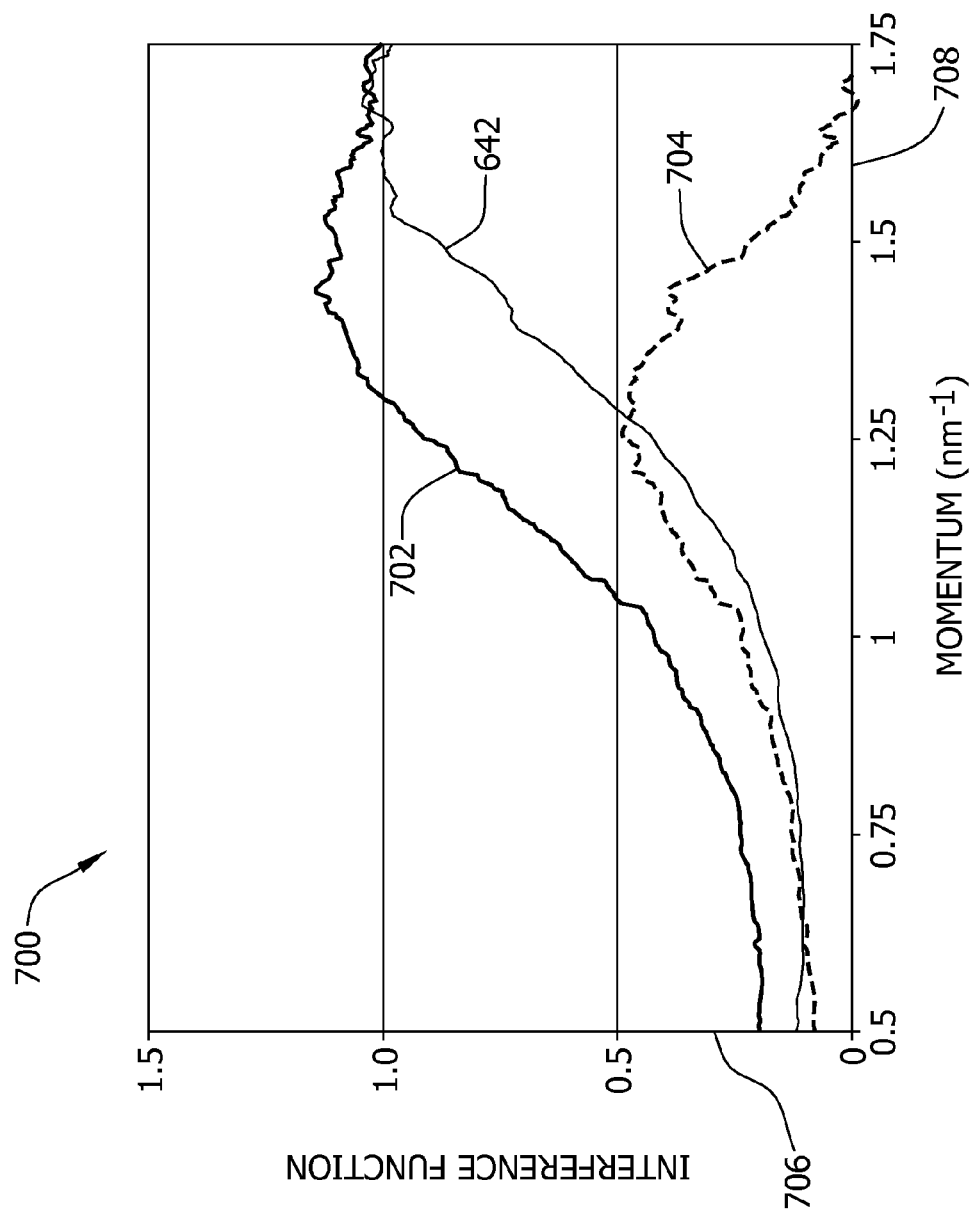

FIG. 9 is a graphical view 700 of an approximated MIF curve 702 for an alcoholic drink, cognac, the approximated MIF curve 742 for water, and a residual MIF curve 704 for cognac derived therefrom using security system 100 (shown in FIG. 1). The alcoholic drink includes an alcohol concentration of approximately 40% by volume.

Graphical view 700 shows an example of determining 510 a second MIF for the second substance that includes determining 512 a second diffraction profile for the second substance, determining 514 a second regression line for the second substance at least partially based on the second diffraction profile, determining 516 a ratio of the second diffraction profile to the second regression line, and generating 518 a residual MIF for the second substance at least partially based on a comparison of the second MIF to first MIF (all shown in FIG. 4). In the exemplary embodiment, method steps 512 and 514 are substantially similar to method steps 504 and 506 (both shown in FIG. 4) as performed for water and described above (shown in FIGS. 6 and 7). Therefore, performance of method steps 512 and 514 for cognac and a diffraction profile and a regression line for cognac are not discussed or shown. Also, in the exemplary embodiment, in a manner similar to that described above for method step 504 for water (shown in FIG. 5), determining 512 a diffraction profile for cognac includes determining a triangular IAM approximation for cognac. Further, in the exemplary embodiment, method step 516 for generating a ratio of the diffraction profile for cognac to the regression line for cognac is the form of approximated MIF curve 702 for cognac is substantially similar to method step 518 for number 2 diesel fuel oil as described above (shown in FIG. 8).

Graphical view 700 includes an ordinate (y-axis) 706 that represents a normalized MIF amplitude in unitless values that at least partially represent a number of photons detected as a function of scattered x-rays within the cognac. Y-axis 706 extends from a value of 0.0 to a value of 1.5. Graphical view 700 also includes an abscissa (x-axis) 708 that represents a momentum of the detected photons in units of inverse nanometers, or $nm^{-1}$. X-axis 708 extends from a value of 0.5 $nm^{-1}$ to a value of 1.75 $nm^{-1}$. As described above, values of x below 0.5 $nm^{-1}$ generate suspect values of y.

Approximated MIF curve 642 for water is determined using the methods described above. Therefore, a first approximated MIF 642 for the first substance, water, is determined by generating diffraction profile 622 (shown in FIG. 6) for the water and then determining a first regression line 624 (shown in FIG. 6) for the water at least partially based on the water's diffraction profile 622. Profile 622 is then divided by regression line 624 to generate approximated MIF curve 642. In one embodiment, approximated water MIF curve 642 used in this process has sufficient counting statistics, that is, a sufficiently high signal-to-noise ratio, and has been accumulated over an extended measurement time period, thereby facilitating accuracy and precision of curve 642. The length of the extended measurement time period is at least partially based on a statistical analysis of the consistency of results obtained over a range of measurement time periods.

Similarly, for a second substance, such as, cognac, a second diffraction profile (not shown) is generated, a second regression line (not shown) is generated using the triangular IAM approximation methods described above, and the second diffraction profile is divided by the second regression line to generate a second approximated MIF curve 702 for the cognac.

Subsequently, a comparison of second approximated MIF curve 702 for the cognac and first approximated MIF curve 642 for the water generates a residual MIF curve 704 via the following equation:

$$R(x) = MIF_{H2O}(x) * \{[S^{subs}_{norm}(x)]/[S^{H2O}_{norm}(x)] - 1\}, \quad \text{Eq. (2)}$$

wherein x represents the momentum transfer variable as described above, R(x) represents residual MIF curve 704, $MIF_{H2O}(x)$ represents the MIF for the first substance (water) as a function of x, $S^{subs}_{norm}(x)$ represents the regression line for the second substance (cognac) at least partially based on the diffraction profile of the cognac as a function of x, and $S^{H2O}_{norm}(x)$ represents regression line 624 for the water at least partially based on diffraction profile 622 of the water as a function of x.

Alternatively, a comparison of second approximated MIF curve 702 for the cognac and first approximated MIF curve 642 for the water generates a residual MIF curve 704 via the following equation:

$$R(x) = MIF_{subs}(x) - MIF_{H2O}(x) \quad \text{Eq. (3)}$$

wherein x is a momentum transfer variable, R(x) represents residual MIF curve 704, $MIF_{H2O}(x)$ represents the MIF for the first substance (water) as a function of x and $MIF_{subs}(x)$ represents the MIF for the second substance (cognac) as a function of x.

Generally, as described above, each of the water MIF and the cognac MIF is individually normalized to unity at larger momentum values, that is, at values of x greater than approximately 1.25 $nm^{-1}$ through approximately 1.5 $nm^{-1}$. Therefore, the generated residual MIF is expected to be approximately zero at large x. Also, each of the water MIF and the cognac MIF has relatively low amplitudes at lower x values, that is, at momentum values less than approximately 1.25 $nm^{-1}$ through approximately 1.5 $nm^{-1}$. Therefore, in general, a residual MIF curve has a low amplitude value at low x values, rises to a peak at moderate x values, and decays to approximately zero at large x values. The residual MIF for water is by definition zero at all x values. The peak-like shape of the residual MIF curve facilitates extraction of features often used for peak evaluation, such features including, without limitation, a curve area, a mean value, a standard deviation, a skew, and a kurtosis.

Upon determination of R(x), that is, residual MIF curve 704, MIF curve 704 is compared to similarly generated residual MIF curves for a plurality of substances. If no match is generated, system 100 notifies a user that no match has been determined. Alternatively, if curve 704 is substantially similar to known residual MIF curves of at least one other substance, the user is alerted to the potential substances that may have been determined.

In general, many liquid substances are aqueous substances that include water as a solvent and another substance as a solute, for example, alcohol in cognac. Removing the effect of water from an XRD profile of the aqueous substance facilitates uniquely identifying the solute within the aqueous substance by substantially isolating and identifying the contribution from the solute. Such improved identification of suspect substances and material classification, particularly for aqueous mixtures, facilitates higher detection rates and lower false alarm rates.

Figure 10:
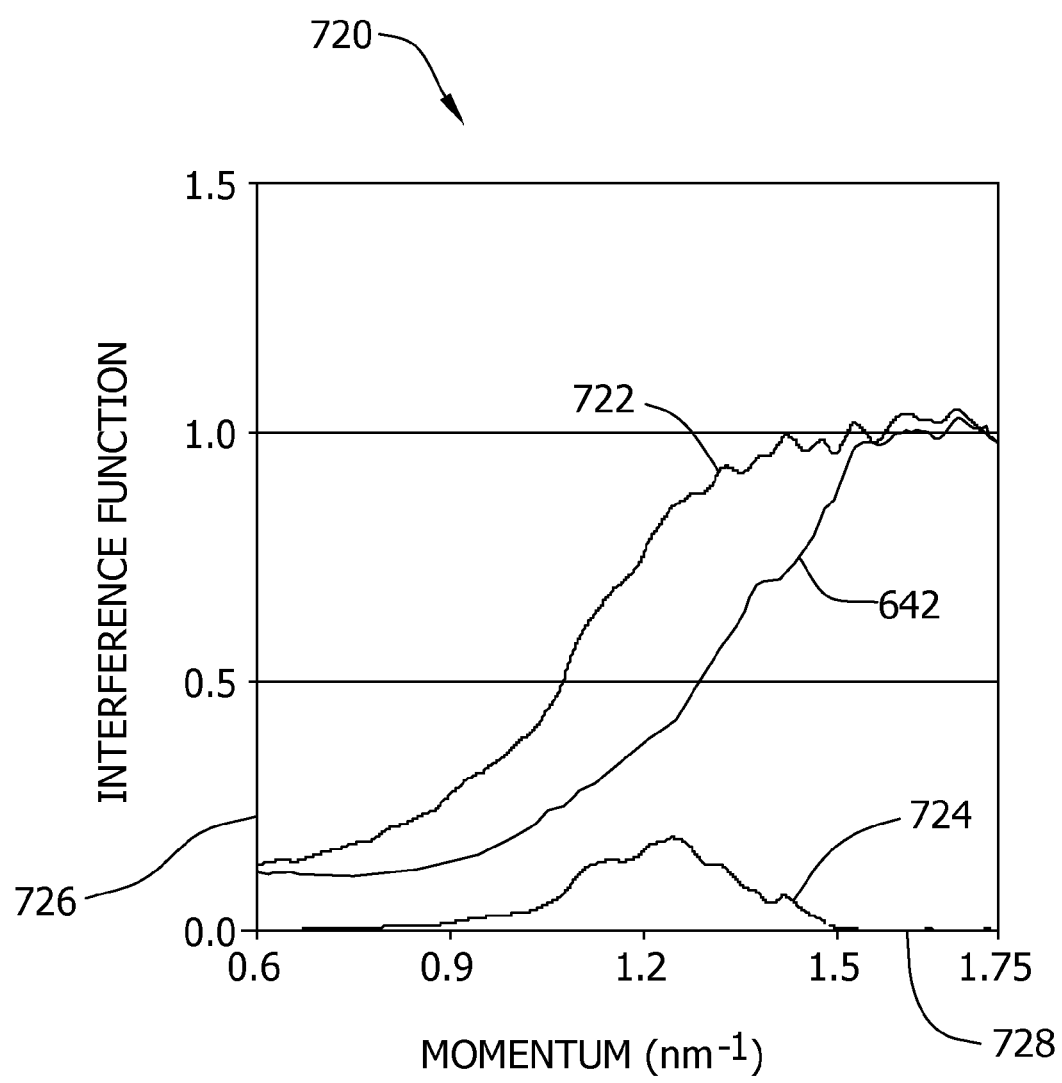

FIG. 10 is a graphical view 720 of an approximated MIF curve 722 for a cola beverage, the approximated MIF curve 642 for water, and a residual MIF curve 724 for the cola beverage derived therefrom using security system 100 (shown in FIG. 1). Graphical view 720 includes an ordinate (y-axis) 726 that represents a normalized MIF amplitude in unitless values that at least partially represent a number of photons detected as a function of scattered x-rays within the cola beverage. Y-axis 726 extends from a value of 0.0 to a value of 1.5. Graphical view 720 also includes an abscissa (x-axis) 728 that represents a momentum of the detected photons in units of inverse nanometers, or $nm^{-1}$. X-axis 328 extends from a value of 0.6 $nm^{-1}$ to a value of 1.75 $nm^{-1}$. As described above, values of x below 0.6 $nm^{-1}$ generate suspect values of y. The methods of generating residual MIF curve 724 for the cola beverage is substantially similar to that method described for generating residual MIF curve 704 for cognac (shown in FIG. 9) with the exception that since a residual MIF value may have either positive or negative values, the resultant R(x) that represents residual MIF curve 724 as determined by either Eq. 2 or Eq. 3 is squared.

Figure 11:
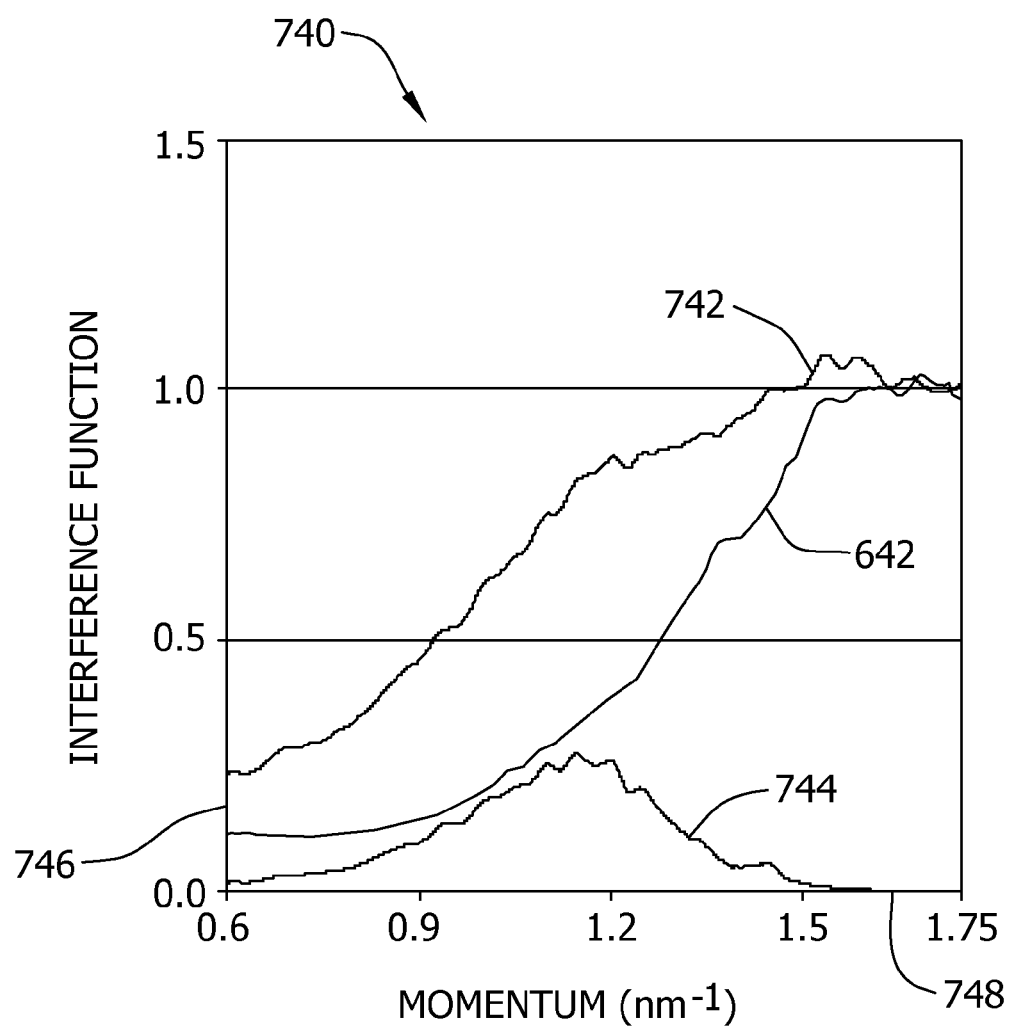

FIG. 11 is a graphical view 740 of an approximated MIF curve 742 for sun cream, approximated curve 642 for water, and a residual MIF curve 744 for the sun cream derived therefrom using security system 100 (shown in FIG. 1). Graphical view 740 includes an ordinate (y-axis) 746 that represents a normalized MIF amplitude in unitless values that at least partially represent a number of photons detected as a function of scattered x-rays within the sun cream. Y-axis 746 extends from a value of 0.0 to a value of 1.5. Graphical view 740 also includes an abscissa (x-axis) 748 that represents a momentum of the detected photons in units of inverse nanometers, or $nm^{-1}$. X-axis 748 extends from a value of 0.6 $nm^{-1}$ to a value of 1.75 $nm^{-1}$. As described above, values of x below 0.6 $nm^{-1}$ generate suspect values of y. The methods of generating residual MIF curve 744 for the sun cream is substantially similar to that method described for generating residual MIF curve 704 for cognac (shown in FIG. 9) with the exception that since a residual MIF value may have either positive or negative values, the resultant R(x) that represents residual MIF curve 744 as determined by either Eq. 2 or Eq. 3 is squared.

Figure 12:
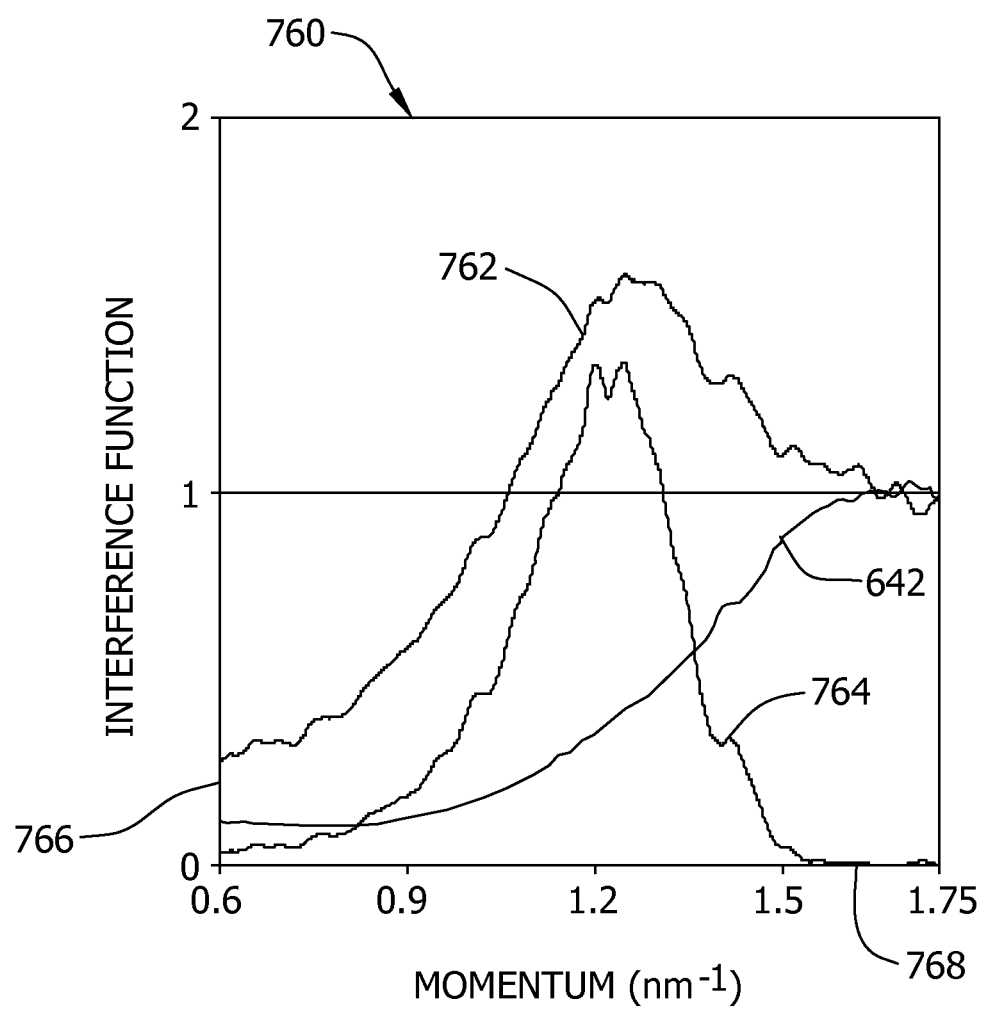

FIG. 12 is a graphical view 760 of an approximated MIF curve 762 for a diesel fuel-water mixture, approximated MIF curve 642 for water, and a residual MIF curve 764 for the diesel fuel-water mixture derived therefrom using security system 100 (shown in FIG. 1). Graphical view 760 includes an ordinate (y-axis) 766 that represents a normalized MIF amplitude in unitless values that at least partially represent a number of photons detected as a function of scattered x-rays within the diesel fuel-water mixture. Y-axis 766 extends from a value of 0.0 to a value of 2.0. Graphical view 760 also includes an abscissa (x-axis) 768 that represents a momentum of the detected photons in units of inverse nanometers, or $nm^{-1}$. X-axis 768 extends from a value of 0.6 $nm^{-1}$ to a value of 1.75 $nm^{-1}$. As described above, values of x below 0.6 $nm^{-1}$ generate suspect values of y. The methods of generating residual MIF curve 764 for the diesel fuel-water mixture is substantially similar to that method described for generating residual MIF curve 704 for cognac (shown in FIG. 9) with the exception that since a residual MIF value may have either positive or negative values, the resultant R(x) that represents residual MIF curve 764 as determined by either Eq. 2 or Eq. 3 is squared.

FIG. 13 is a table 780 of central moments of a plurality of substances and the associated residual MIFs derived using security system 100 (shown in FIG. 1). As described above, use of residual MIFs emphasizes characteristics of additives that would otherwise be overwhelmed by the large background signal of water. Therefore, use of such residual MIFs enhances the detection rate for threat substances while reducing the false alarm rate for innocuous materials. Moreover, residual MIFs tend to peak at moderate momentum values while decreasing through low and high values of x. The peak-like shape of the residual MIF curve facilitates extraction of features often used for peak evaluation, such features including, without limitation, a curve area, a mean value, a standard deviation, a skew, and a kurtosis.

The first five moment features extracted from the residual MIF functions are shown in table 780. The columns of table 780 are arranged in order of increasing area under the residual MIF, which is generally proportional to the amount of additive present in the water. The zero moment represents an area under the residual MIF curve. The fuel-water mix is particularly notable in that it has a value for the zero moment far greater than that for cola, cognac, and sun cream. The first moment represents a mean value of the amplitude values that define the residual MIF curve. The second moment represents a standard deviation associated with a width of the residual MIF curve. The third moment represents a skew of the residual MIF curve. The fourth moment represents a kurtosis of the residual MIF curve.

Therefore, in general, these moments provide sufficient information for classifying the substances in groups relevant to security screening, with cola, cognac, and sun cream being relatively harmless and a fuel-water mixture indicating a potentially dangerous substance. Should further discrimination be desired, these features can be supplemented by, for example, but without limitation, a cross-correlation coefficient, i.e., a measure of similarity of form between the measured residual MIF and that stored in a library.

The above-described methods and systems facilitate effective and efficient operation of a security system by increasing detection rates of contraband substances and decreasing false alarm rates of non-contraband substances. The methods and systems derive molecular interference functions (MIFs) from x-ray diffraction (XRD) profiles of liquids, amorphous substances, and gel substances. More specifically, the methods and systems record an XRD profile of a substance that is subsequently normalized with a best-fit regression line that is part of an Independent Atom Model (IAM) triangular approximation. In one embodiment, the methods and systems calculate a ratio of the values associated with respect to the XRD profile and the regression line and forms an approximation for the associated MIF for the substance. Moreover, the self-normalization aspects of the methods described herein normalizes features of the XRD profile in the lower band of momenta that contains significant signal data against features of the XRD profiles in a higher band of momenta that contains significant noise data. In addition an approximated MIF of water is subtracted from an approximated MIF of a substance under investigation to yield a residual MIF. Utilization of the residual MIF further improves the signal-to-noise ratio, therein further improving material classifications, particularly for aqueous mixtures, with increased accurate detection rates and decreased false alarm rates, with little additional consumption of computation resources and expenditure of time.

Exemplary embodiments of methods and x-ray screening devices for operating a security system are described above in detail. The methods and x-ray screening devices are not limited to the specific embodiments described herein, but rather, components of systems and/or steps of the methods may be utilized independently and separately from other components and/or steps described herein. For example, the methods may also be used in combination with other security systems and methods, and are not limited to practice with only the security systems as described herein. Rather, the exemplary embodiment can be implemented and utilized in connection with many other security system applications.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for identifying a substance, said method comprising:
   determining a first molecular interference function (MIF) for a first substance;
   determining a second MIF for a second substance;
   generating a residual MIF at least partially based on a comparison of the second MIF to the first MIF; and
   identifying the substance based on the residual MIF.

2. A method in accordance with claim 1, wherein determining a first MIF for a first substance and determining a second MIF for a second substance comprise determining a MIF for one of a liquid substance, an amorphous substance, and a gel substance.

3. A method in accordance with claim 2, wherein determining a first MIF for a first substance comprises determining a MIF for water.

4. A method in accordance with claim 1, wherein determining a first MIF for a first substance comprises:
   determining a first diffraction profile for the first substance;
   determining a first regression line for the first substance at least partially based on the first diffraction profile; and
   determining a ratio of the first diffraction profile to the first regression line.

5. A method in accordance with claim 1, wherein determining a second MIF for a second substance comprises:
   determining a second diffraction profile for the second substance;
   determining a second regression line for the second substance at least partially based on the second diffraction profile; and
   determining a ratio of the second diffraction profile to the second regression line.

6. A method in accordance with claim 1, wherein generating a residual MIF at least partially based on a comparison of the second MIF to the first MIF comprises finding a comparison of the second MIF to the first MIF by determining a ratio of a regression line for the second substance to a regression line for the first substance, the first substance being water.

7. A method in accordance with claim 6, wherein finding a comparison of the second MIF to the first MIF by determining a ratio comprises finding a quotient using division to divide a regression line value for the second substance by a value that includes unity subtracted from a regression line value for the first substance.

8. A method in accordance with claim 7, wherein generating a residual MIF at least partially based on a comparison of the second MIF to the first MIF comprises finding a product using multiplication of the ratio by the MIF for water.

9. A method in accordance with claim 6, wherein generating a residual MIF at least partially based on a comparison of the second MIF to the first MIF further comprises determining the first MIF and the second MIF as a function of a momentum transfer variable.

10. A method in accordance with claim 1, wherein generating a residual MIF at least partially based on a comparison of the second MIF to the first MIF comprises finding a comparison of the second MIF to the first MIF by determining a difference by subtracting the first MIF from the second MIF.

11. A method of operating a security system, said method comprising:
   irradiating a substance with x-rays;
   determining momentum transfer values of x-rays scattered from the substance;
   generating a residual molecular interference function (MIF) for the substance that is at least partially based on the momentum transfer values; and
   identifying the substance based on the generated residual MIF for the substance.

12. A method in accordance with claim 11, wherein generating a residual MIF for the substance comprises:
   generating a MIF for the substance that is based on the momentum transfer values; and
   comparing the MIF for the substance to a MIF standard.

13. A method in accordance with claim 12, wherein comparing the MIF for the substance to a MIF standard comprises comparing the MIF for the substance to a MIF for water.

14. A method in accordance with claim 11, wherein identifying the substance based on the generated residual MIF for the substance comprises comparing the generated residual MIF for the substance to a plurality of residual MIFs generated for a plurality of substances.

15. A substance determination system, said system comprising:
   a processor coupled to at least one x-ray detector element, said processor programmed to:
      determine at least one of a first molecular interference function (MIF) for a first substance and determine a second MIF for a second substance; and
      generate a residual MIF at least partially based on a comparison of said second MIF to said first MIF; and
   a display device coupled to said processor, said display device configured to identify the second substance based on said residual MIF; and
   at least one memory device coupled to said processor, said memory device configured to store at least one of said first MIF, said second MIF, and said residual MIF.

16. A substance determination system in accordance with claim 15, wherein said processor programmed to determine a first MIF for a first substance comprises said processor programmed to determine a first MIF for water.

17. A substance determination system in accordance with claim 16, wherein said processor programmed to determine at least one of a MIF for water and determine a second MIF for a second substance comprises a processor programmed to:
   determine at least one of a first diffraction profile for water and a second diffraction profile for the second substance;
   determine at least one of a first regression line for water at least partially based on the first diffraction profile and a second regression line for the second substance at least partially based on the second diffraction profile; and
   determine at least one of a ratio of the first diffraction profile to the first regression line and a ratio of the second diffraction profile to the second regression line.

18. A substance determination system in accordance with claim 15, wherein said display device configured to identify the second substance based on said residual MIF comprises a display device configured to display a comparison of said second MIF to a MIF for water, wherein the comparison is unique to the second substance.

19. A substance determination system in accordance with claim 18, wherein said processor is programmed to compare the second MIF and the MIF for water by at least one of:
   determining a ratio of a regression line for the second substance to the regression line for water; and
   subtracting the MIF for water from the second MIF.

20. A substance determination system in accordance with claim 15, wherein said display device is further configured to display at least one of a warning and alert as a function of the composition of the second substance.

21. A security system comprising:
   an x-ray source configured to generate x-rays;

a detector configured to detect primary and coherent scatter after the x-rays pass through a substance; and a processor coupled to said detector, said processor programmed to:

determine at least one of a first molecular interference function (MIF) for a first substance and determine a second MIF for a second substance; and generate a residual MIF at least partially based on a comparison of said second MIF to said first MIF; and a display device coupled to said processor, said display device configured to identify the second substance based on said residual MIF.

22. A security system in accordance with claim 21, wherein said processor programmed to determine a first MIF for a first substance comprises said processor programmed to determine a first MIF for water.

23. A security system in accordance with claim 22, wherein said processor programmed to determine at least one of a MIF for water and determine a second MIF for a second substance comprises a processor programmed to:

determine at least one of a first diffraction profile for water and a second diffraction profile for the second substance;

determine at least one of a first regression line for water at least partially based on the first diffraction profile and a second regression line for the second substance at least partially based on the second diffraction profile; and determine at least one of a ratio of the first diffraction profile to the first regression line and a ratio of the second diffraction profile to the second regression line.

24. A security system in accordance with claim 21, wherein said display device configured to identify the second substance based on said residual MIF comprises a display device configured to display a comparison of said second MIF to a MIF for water, wherein the comparison is unique to the second substance.

25. A security system in accordance with claim 24, wherein said processor is programmed to compare the second MIF and the MIF for water by at least one of:

determining a ratio of a regression line for the second substance to the regression line for water; and subtracting the MIF for water from the second MIF.

26. A security system in accordance with claim 21, wherein said display device is further configured to display at least one of a warning and alert as a function of the composition of the second substance.

* * * * *